United States Patent [19]

Touyama et al.

[11] 4,232,159

[45] Nov. 4, 1980

[54] NITROGEN-CONTAINING MONOTERPENE DERIVATIVES

[75] Inventors: Ryousuke Touyama, Kobe; Hiroyuki Inouye, Kyoto; Tetsuro Shingu, Nishinomiya; Yoshio Takeda, Tokushima; Takeshi Ikumoto, Kobe; Hidetoshi Okuyama; Osamu Yamamoto, both of Kobe, all of Japan

[73] Assignee: Taito Co., Ltd., Tokyo, Japan

[21] Appl. No.: 953,275

[22] Filed: Oct. 20, 1978

[51] Int. Cl.$^3$ ............................................ C07D 221/02
[52] U.S. Cl. ................................................... 546/112
[58] Field of Search ........................................ 546/112

[56] References Cited

U.S. PATENT DOCUMENTS 3,963,722  6/1976  Curran .................................. 546/112

FOREIGN PATENT DOCUMENTS 46-4872169 12/1971 Japan ........................................ 546/112
52-13971   4/1977 Japan ........................................ 546/112
53-53934  10/1978 Japan ........................................ 546/112

OTHER PUBLICATIONS

J. Org. Chem., 25 2174 (1960); 26 1192 (1961).
Tetrahedron Letters No. 50, 5125 (1972), No. 28, 2347 (1969).
Chem. Pharm. Bull. (Japan) 21 (2684)(1973), (Japan) 24 (2644)(1976).
Phytochemistry 13 2219 (1974).
Planta Medica 28 109 (1975).

Primary Examiner—Henry R. Jiles
Assistant Examiner—Robert C. Whittenbaugh
Attorney, Agent, or Firm—Fleit & Jacobson

[57] ABSTRACT

Novel nitrogen-containing monoterpene derivatives having pyrindine skeleton synthesized by, for example, substitution of an oxygen atom in an iridoid skeleton for a nitrogen atom as low toxic and efficient dyestuffs. Their pharmacological effects are expected.

1 Claim, 46 Drawing Figures

FIG. 4-1
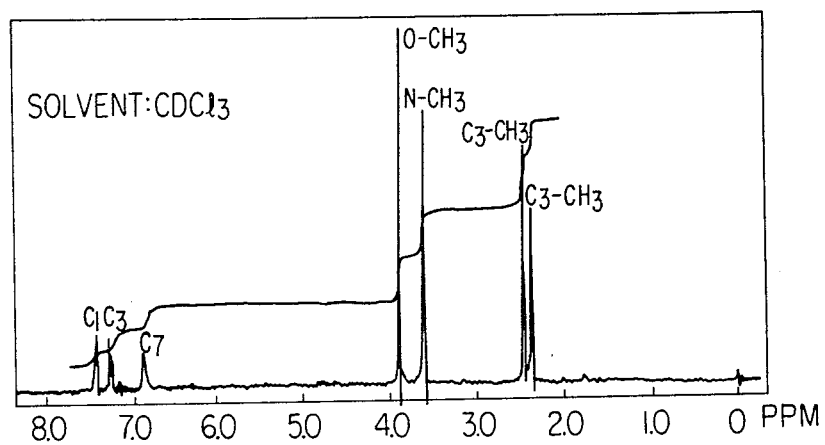
FIG. 4-2
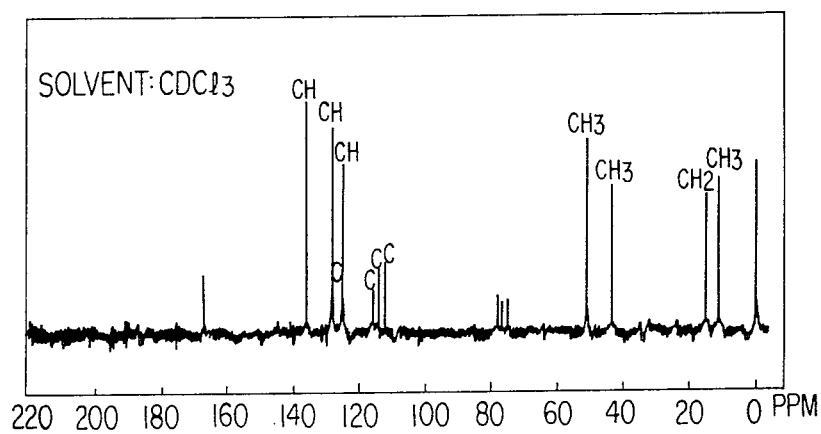
FIG. 4-3
FIG. 4-4
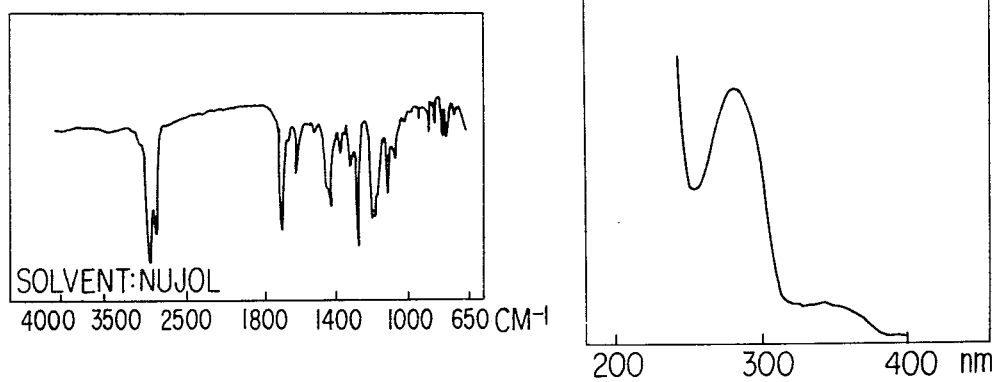

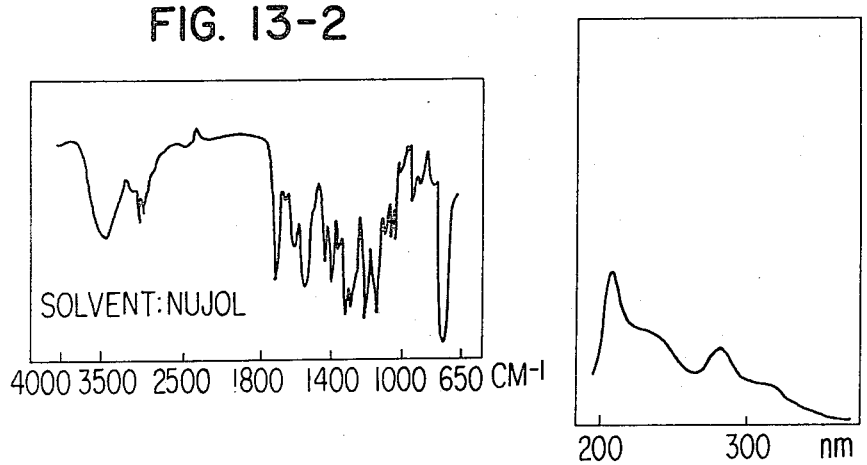
FIG. 13-2
FIG. 13-3
SOLVENT: NUJOL
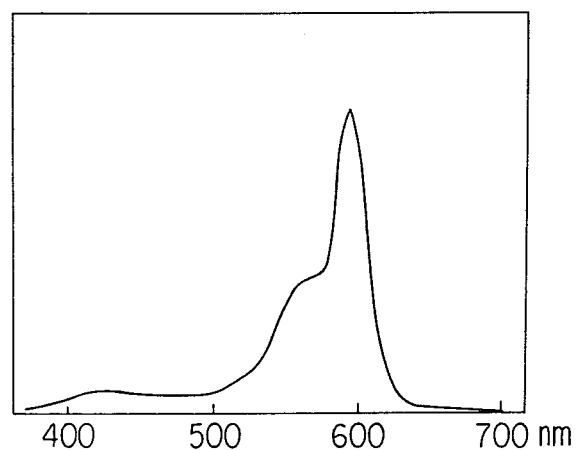
FIG. 13-4
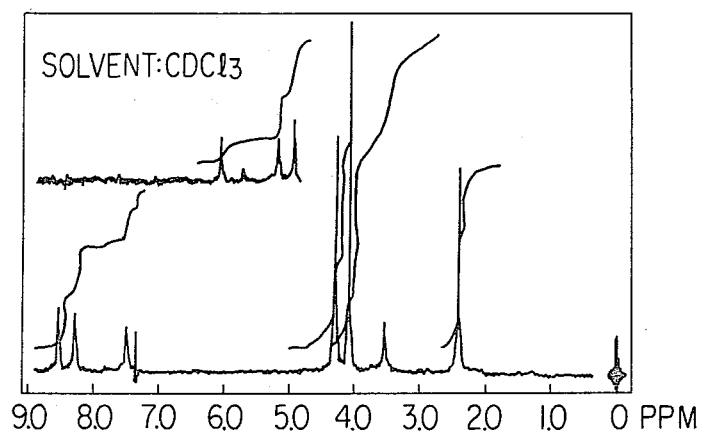
FIG. 14-1
SOLVENT: CDCl₃

NITROGEN-CONTAINING MONOTERPENE DERIVATIVES

BACKGROUND OF THE INVENTION

The present invention relates to nitrogen-containing monoterpene derivatives, especially, to novel nitrogen-containing monoterpene derivatives having a pyrindine skeleton synthesized by, for example, substitution of an oxygen atom in a iridoid skeleton for a nitrogen atom.

Various studies have been directed toward nitrogen-containing monoterpene derivatives having a pyrindine skeleton and processes for synthesizing these derivatives have already been reported. However, none of these processes utilizes the process of this invention wherein an oxygen atom in n iridoid skeleton is replaced with a nitrogen atom. It has been known that iridoid glycosides and aglycones occur in plants, for example, in large amounts in Gardenia jasminoides Ellis, Genipa americana L. etc. of Rubiaceae. It has been said that Gardenia jasminoides Ellis exhibits physiological activities such as purgative, antidotal and antiinflammatory effects and that Genipa americana L. exhibits an antituberculosis effect. The inventors have disclosed that aglycones of irodoid glycosides react with primary amino group-containing substances to form dyestuffs (Japanese Patent Application Nos. 77136/1974 and 130131/1975). However, the chemical structures of components constituting the dyestuffs have not yet been elucidated. The inventors have perfected the present invention upon conducting further investigations on the properties of iridoid glycosides and aglycones thereof and also on the products of reaction of iridoid glycosides or their aglycones with primary amino group-containing substances.

DESCRIPTION OF THE INVENTION

This invention provides novel nitrogen-containing monoterpene derivatives of general formulae I, II, III, IV and V. This invention further provides polymers as well as substances having various visible absorption characteristics which were produced by dehydrogenative polymerization or oxidation of these novel nitrogen-containing monoterpene derivatives. These compounds can be used not only as mere dyestuff intermediates or dyestuffs themselves but also as reagents for analysis of pharmacological effects of iridoids and pyrindine derivatives, as pharmaceuticals and also as intermediates for the synthesis of useful pyrindine compounds.

Aglycones obtainable by hydrolysis of iridoid glycosides are very reactive. When they are reacted with primary amino group-containing compounds, an oxygen atom in the aglycone is easily replaced with a nitrogen atom of the primary amino group. For example, nitrogen-containing six-membered rings of the following formulae I, II, III, IV and V are thus formed:

[Aglycone] + [Primary amino group-containing compound] → [Novel nitrogen-containing monoterpene derivative]

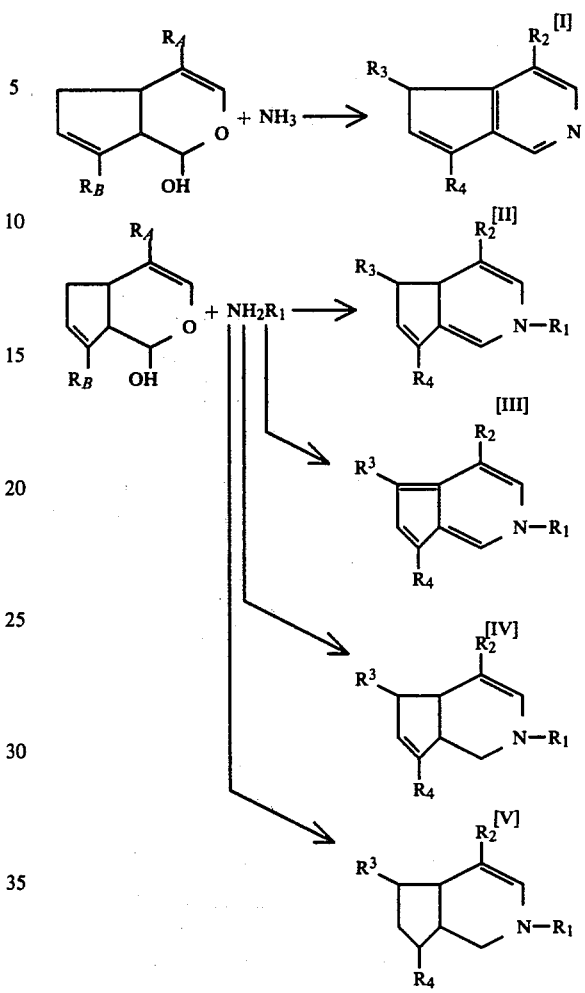

wherein $R_1$ represents a residue of primary amino group-containing compound, $R_2$ represents —CHO, —COOH, or —COOR (R being an alkyl group), $R_3$ represents a group selected from the group consisting of hydrogen and lower alkyl groups, $R_4$ represents hydrogen, lower alkyl groups, —CH$_2$OH and —CHO, $R_A$ in aglycone represents a group selected from the group consisting of —CHO, —COOH and —COOR and $R_B$ represents a group selected from the group consisting of —CH$_2$OH and —CHO.

Substituents $R_1$, $R_2$, $R_3$ and $R_4$ in compounds I, II, III, IV and V of the present invention can be easily transformed according to the starting iridoid compounds and primary amino group-containing compounds to be incorporated therein and the reaction conditions. Many of these compounds are formed directly or indirectly by reaction of an iridoid aglycone with a primary amino group. Because they are very reactive, compounds formed directly by, for example, oxidation-reduction reaction of these compounds or indirectly via an intermediate are related to one another. For example, if an iridoid aglycone genipin is reacted with aqueous ammonia, compound (1) corresponding to a product of general formula I can be obtained:

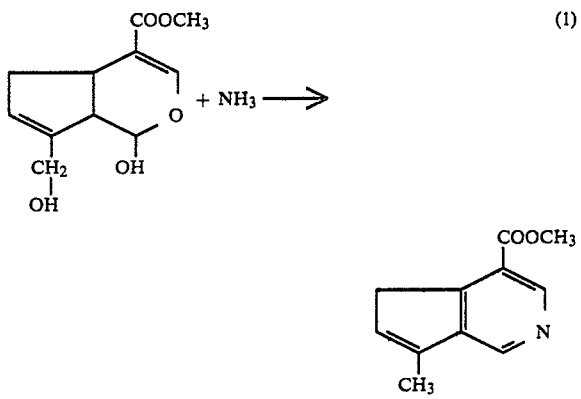

(1)

If genipin is reacted with methylamine in the absence of oxygen, compound (2) corresponding to a product of general formula II can be obtained.

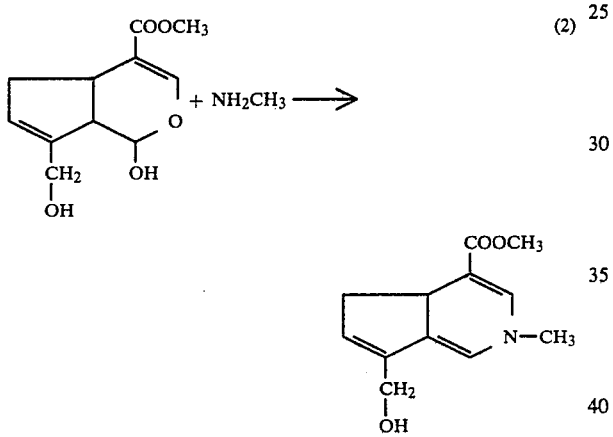

(2)

If compound (2) of general formula II is dissolved in an acidic aqueous solution and then extracted with an organic solvent under alkaline condition, compound (3) corresponding to a product of general formula III can be obtained.

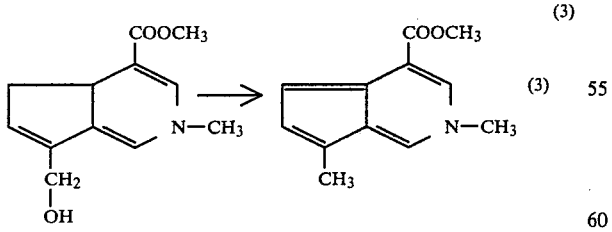

(3)

If compound (2) of general formula II is dissolved in an alcohol and the solution is heated for a long period of time in the absence of oxygen, compound (4) corresponding to a product of general formula III can be obtained.

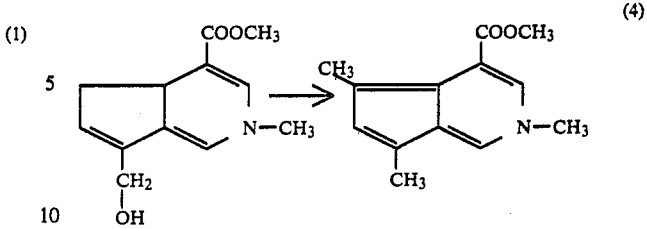

(4)

If compound (4) corresponding to a compound of general formula III is reduced, compound (5) corresponding to a product of general formula V can be obtained.

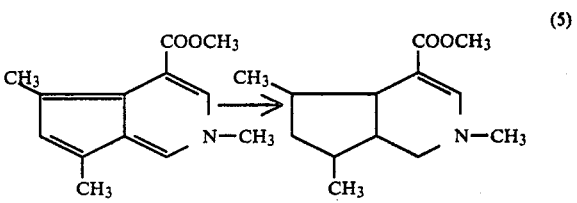

(5)

If genipin is reacted with methylamine in the absence of oxygen under heating for 4 hours, compounds (3) and (4) corresponding to products of general formula III can be obtained simultaneously.

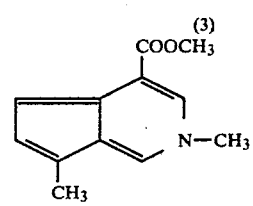

(3)

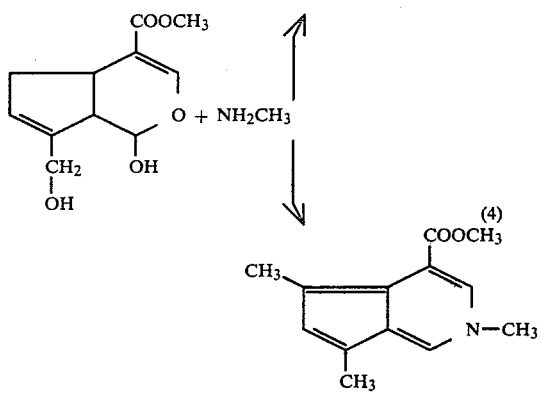

(4)

These products represented by general formulae I, II, III, IV and V are utilizable not only as dyestuff intermediates but also as intermediates for the synthesis of various substances owing to their specific reactivities.

As compounds represented by general formulae I, II, III, IV and V contain a nitrogen atom to form the heterocyclic six-membered ring and the adjacent five-membered ring, they form various products such as polymers including dimers and trimers by combination of highly reactive $C_1$, $C_6$ and $C_8$ as well as substituents $R_3$ and $R_4$ on these carbon atoms. For example, polymers such as dimers and trimers shown by the following chemical formulae (6), (7), (8) and (9) are obtainable by heating an iridoid aglycone together with a primary amino group-containing substance or by heating a compound of general formula II alone in a proper solvent in the absence of oxygen.

Further, various polymers exhibiting maximum absorption in the visible region can be obtained by heating a solution of an iridoid aglycone and a primary amino group-containing compound or by heating a solution of a compound of general formula I, II, III, IV or V in the presence of oxygen. For example, stirring a solution of a compound of general formula II in alcohol in the air yields compound (10) having maximum absorptions in visible region. Stirring an ethanolic solution of a compound of general formula III in the air while heating yields compound (11) having maximum absorption in the visible region,

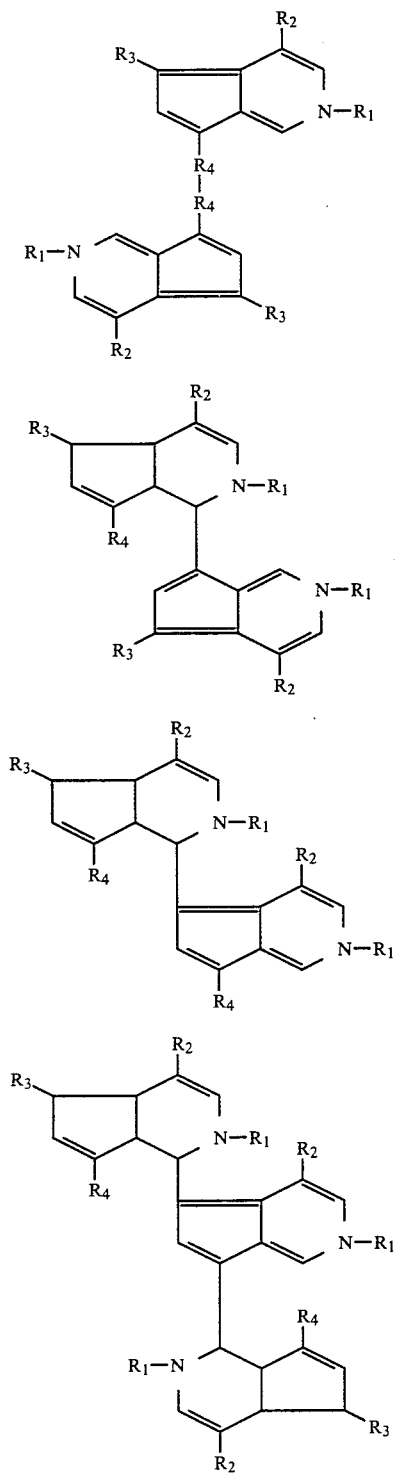

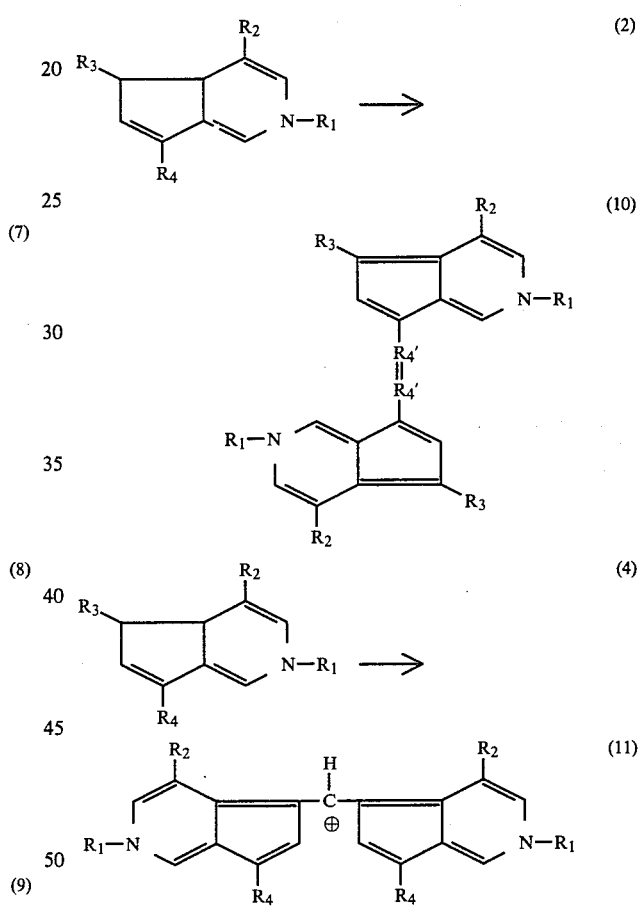

where $R'_4$ represents a lower alkylidene group.

These polymers can be utilized in various ways by converting them into various forms by further chemical reactions. For example, they can be converted to compounds of lower molecular weight by cleavage of bonds and they can also be polymerized again. Further, the extention of the conjugated system of these compounds by dehydrogenative oxidation or repolymerization gives compounds having maximum absorption in the visible region. For example, dimers (7) and (8) and monomer (3) can be formed by heating trimer (9) while stirring in the absence of oxygen.

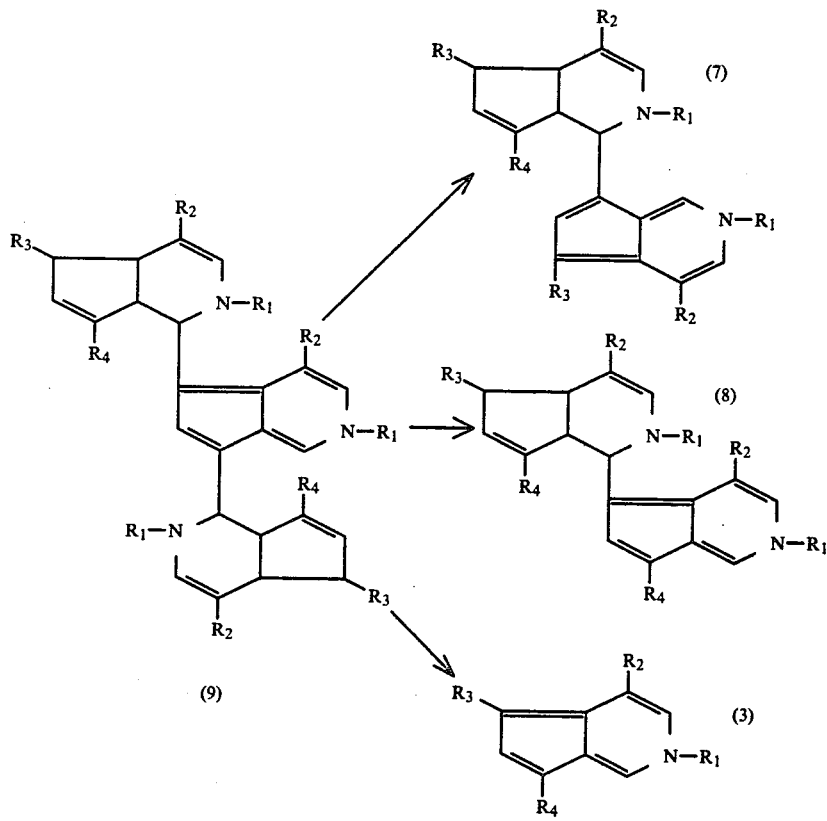

Further, trimer (9) and monomer (3) can be formed by heating the dimer (7) while stirring in the absence of oxygen.

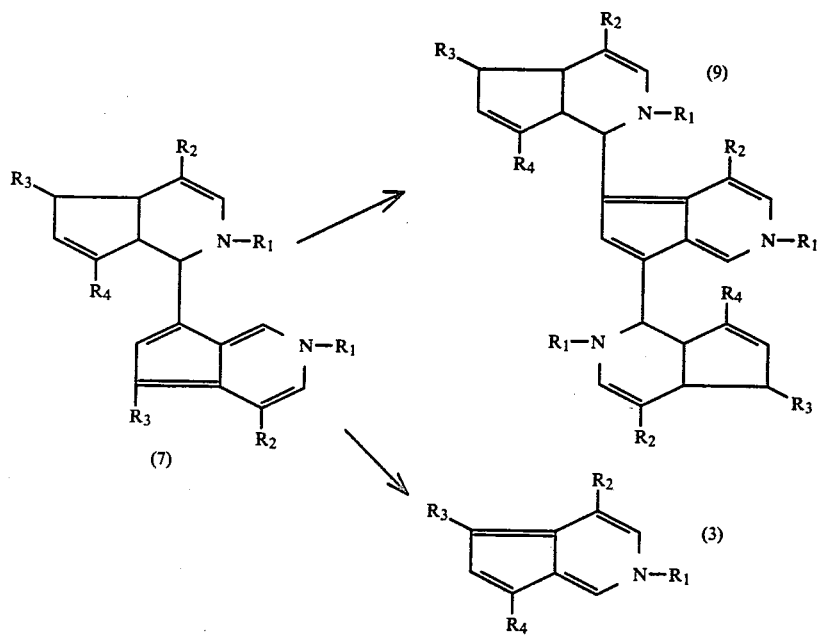

These dimers and trimers can form compounds having maximum absorption in the visible region by extention of the conjugated system through oxidation in the air or re-polymerization in the same manner as in the case of compounds represented by general formulae I, II, III, IV and V. For example, dimer (6) obtained from a compound represented by general formula II is subjected to dehydrogenation by stirring in the presence of oxygen to form blue compound (10).

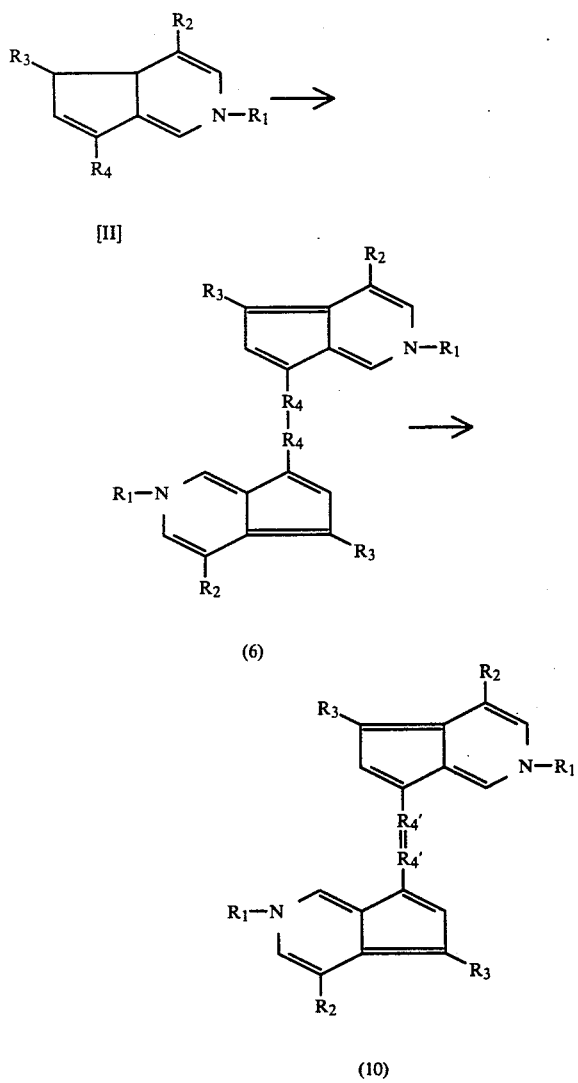

As the reactivities of these compounds are greatly influenced by the lone pair of electrons of nitrogen in the heterocyclic six-membered ring, various compounds can be formed by controlling the lone pair of electron.

Nitrogen-containing monoterpene derivatives of general formulae I, II, III, IV and V of the present invention can be prepared in the form of compounds of desired chemical formuale wherein $R_1$ varies depending on the primary amine used, $R_2$ varies depending on the starting compound selected and $R_3$ and $R_4$ may be hydrogen or a lower alkyl group depending on the starting compound selected and the reaction cnditions. Further, dimers, trimers and higher polymers can also be formed by polimerizing the compounds having these various groups. Furthermore, various derivatives can also be obtained by chemical modification of the products. For example, it is possible to form colored materials through oxidative polymerization by oxidizing them. As the colored materials thus obtained may have various substituents $R_1$, $R_2$, $R_3$ and $R_4$ and, consequently, have different maximum absorption wave lengths and physico-chemical properties, wide utilization of these colored substances as dyestuffs and pigments can be expected. The above described chemical reaction can be utilized also for the detection of primary amino group-containing substances.

Several pharmacological effects such as sedative effects of pyrindine derivatives have hitherto been reported. Profitable effects including pharmacological effects of nitrogen-containing monoterpene derivatives which can be synthesized according to this invention are also highly expectable through appropriate modifications of $R_1$, $R_2$, $R_3$, $R_4$, etc.

Thus, novel utilities of the derivatives of the present invention can be developed without difficulty.

BRIEF DESCRIPTION OF THE DRAWINGS

The accompanying drawings show proton nuclear magnetic resonance (PMR), $C^{13}$ nuclear magnetic resonance (CMR), infrared absorption (IR), ultraviolet absorption (UV), and visible absorption spectra (VIS) of the novel nitrogen-containing monoterpene derivatives of this invention. FIG. 2-1 shows PMR of a derivative obtained in Example II. FIGS. 3-1, -2, -3, and -4 show PMR, CMR, IR and UV of a derivative obtained in Example III. FIGS. 4-1, -2, -3 and -4 show PMR, CMR, IR and UV of a derivative obtained in Example IV. FIG. 5-1 shows PMR of a derivative obtained in Example V. FIGS. 6-1, -2, and -3 show PMR, IR, and uv of a derivative obtained in Example VI. FIG. 7-1 shows PMR of a derivative obtained in Example VII. FIGS. 8-1, -2, -3 and -4 show PMR, CMR, IR and UV of a compound VIII-2 obtained in Example VIII. FIGS. 8-5, -6, -7 and -8 show PMR, CMR, IR and UV of a compound VIII-3 obtained in Example VIII. FIGS. 9-1 and -2 show PMR and IR of a derivative obtained in Example IX. FIGS. 10-1, -2, -3 and -4 show PMR, CMR, IR and UV of a derivative obtained in Example XI. FIGS. 11-1, -2, -3 and -4 show PMR, CMR, IR and UV of a derivative obtained in Example XII. FIGS. 12-1, -2, -3 and -4 show PMR, CMR, IR and UV of a product XIII-3 obtained in Example XIII. FIGS. 13-1, -2, -3 and -4 show PMR, IR, UV and VIS of a derivative obtained in Example XVII. FIGS. 14-1, -2, -3, -4 and -5 show PMR, CMR, IR, UV and VIS of a derivative obtained in Example XVIII.

Example I

A mixture of 452 mg of genipin and 0.5 ml or 28% aqueous ammonia was dissolved in 40 ml. of a mixture of McIlvaine buffer solution (pH 7.2) and ethanol (1:1). After heating the mixture at 70° C. under argon, the solvent was evaporated under reduced pressure and the residue was subjected to extraction with $CHCl_3$ (50 ml.×3). The $CHCl_3$ extract was washed with water and then the solvent was evaporated under reduced pressure to yield 430 mg of a colorless syrupy residue.

The residue was purified on a silica gel column with ether as the developing solvent. Eluate was fractionated and the solvent was evaporated under reduced pressure to yield colorless needles. The structural formula of this compound is as follows:

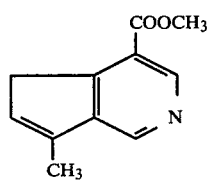

Figure 1:
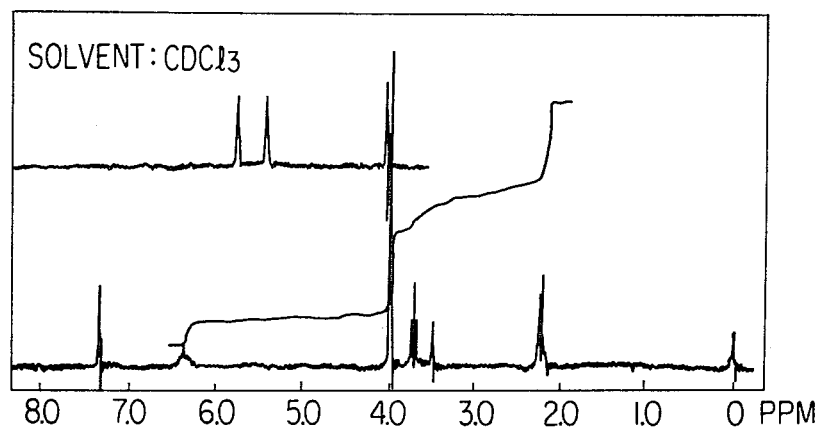
FIG. 1-1 shows PMR of a derivative obtained in Example I.

PMR: FIG. 1-1 MS (Mass spectrum parent peak) m/e 189

EXAMPLE II

A mixture of 452 mg (2 mM) of genipin and 402 mg (6 mM) of methylamine hydrochloride was dissolved in 40 ml. of a mixture of McIlvaine buffer solution (pH 7.2) and ethanol (1:1). After stirring at room temperature under argon for 4 hours, the reaction mixture was extracted with chloroform. Evaporation of the solvent yielded 420 mg of a red oily substance.

The structural formula of the product is shown as follows;

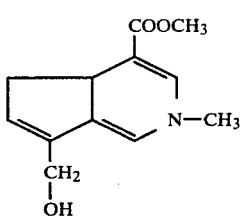

PMR: FIG. 2-1

Example III

A mixture of 452 mg of genipin and 201 mg of methylamine hydrochloride was dissolved in 40 ml. of a mixture of McIlvaine buffer solution (pH 7.2) and ethanol (1:1). The solution was stirred in an open system at room temperature for one hour and then the solvent was evaporated under reduced pressure. The residue was extracted with benzene. The benzene extract was washed with water and then dried. The solvent was evaporated under reduced pressure to yield 300 mg of a red syrupy residue. The residue dissolved in 30 ml. of benzene was extracted with 30 ml. of 1 N hydrochloric acid. The resulting hydrochloric acid solution was made alkaline with 50 ml. of 1 N NaOH and then extracted with benzene. The benzene extract was washed with water and dried. The solvent was evaporated under reduced pressure to yield 150 mg of a red syrupy residue. The residue was purified by chromatography on a Sephadex LH 20 (trade name) column with methanol as the developing solvent to yield 30 mg of red needle.

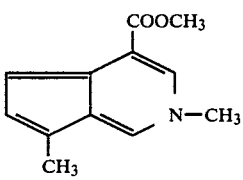

Figures 1, 2:
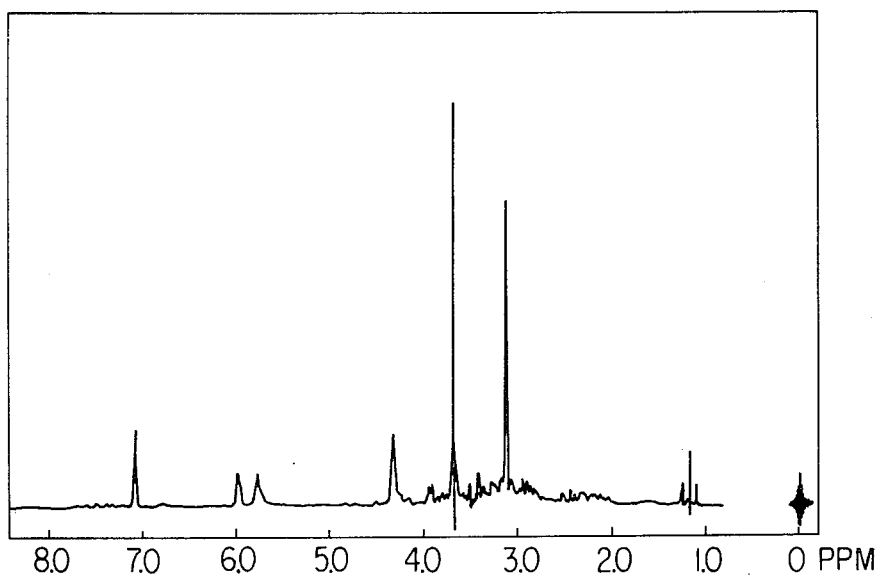
Figures 1, 3:
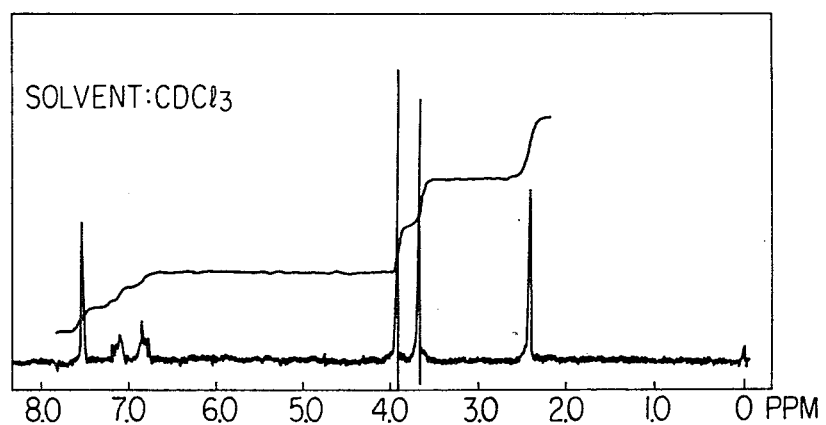
Figures 2, 3:
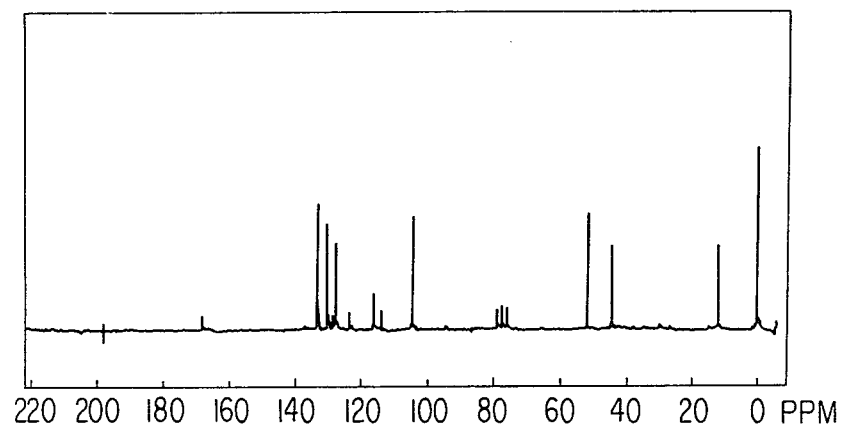
Figure 3:
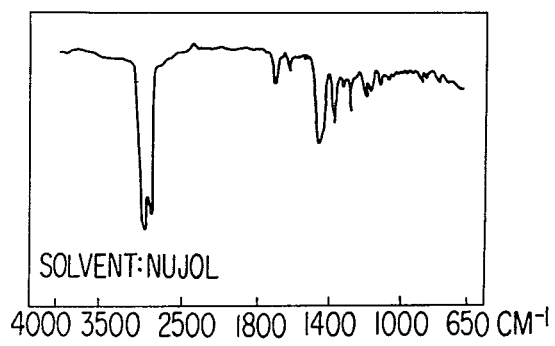
Figures 3, 4:
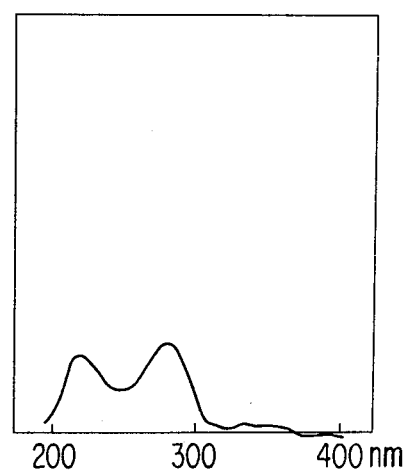

Properties of the compound are given as follows:
MP (melting point): 148°–149.5° C.
PMR: FIG. 3-1
CMR: FIG. 3-2
IR: FIG. 3-3
UV: FIG. 3-4
MS: m/e 203
$\lambda_{max}^{EtOh}$ 284 nm (log $\epsilon$=4.31)

Example IV

A mixture of 904 mg of genipin and 268 mg of methylamine hydrochloride dissolved in 60 ml. of a mixture of McIlvaine buffer solution (pH 7.2) and ethanol (1:1) was heated to 60°–70° C. under nitrogen stream for two hours. Then, the solvent was distilled off under reduced pressure. The residue was extracted with chloroform. The extract was washed with water and then dired. Thereafter, the solvent was evaporated under reduced pressure to give 400 mg of a red syrupy residue. The residue was chromatographed on silica gel with chloroform as the developing solvent. The chloroform eluates were combined and concentrated to give 200 mg of the residue which was purified on a column of Sephadex LH 20 with methanol as the developing solvent to yield 50 mg of red needles.

The structure of the compound is shown by the following formula:

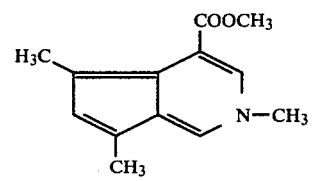

Properties of this compound are given as follows:
MP: 138°–139° C.
PMR: FIG. 4-1
CMR: FIG. 4-2
IR: FIG. 4-3
UV: $\lambda_{max}^{EtOh}$ 283 nm (log $\epsilon$=4.13) FIG. 4—4
MS: m/e 217

Example V

A mixture of 900 mg of genipin and 450 mg of ethylamine hydrochloride was treated in the same manner as in the case of Example IV to yield 60 mg of red needles.

The compound has the following structural formula:

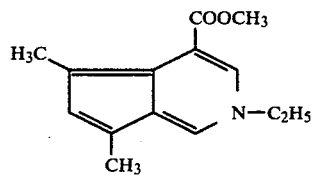

Figures 1, 5:
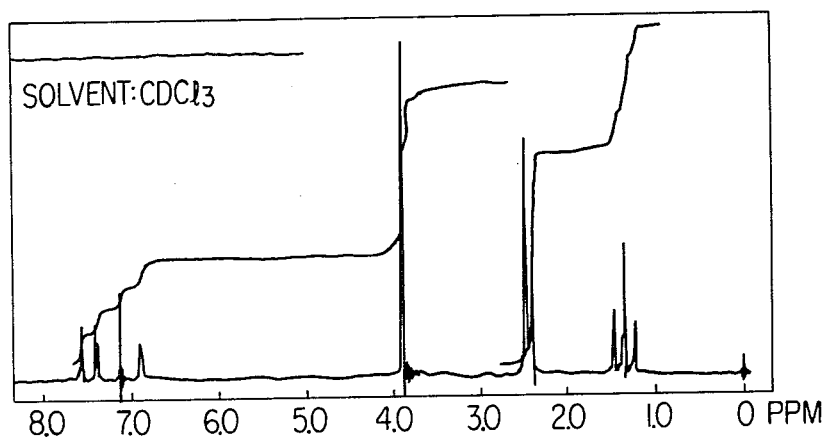

Properties of the compound are given as follows:
PMR: FIG. 5-I
MS: m/e 231

Example VI

A mixture of 904 mg of genipin and 350 mg of glycine methyl ester hydrochloride was treated in the same manner as in the case of Example IV to yield 70 mg of a red oily compound.

The compound has the following structural formula:

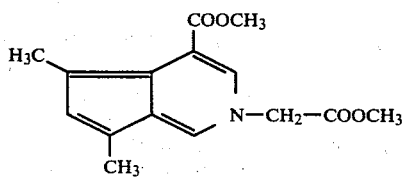

Figures 1, 6:
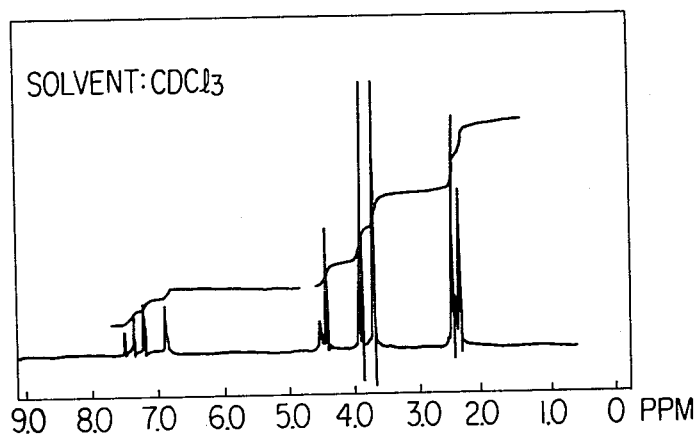
Figures 2, 6:
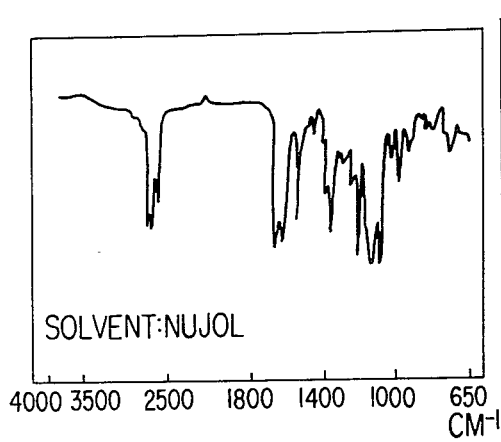
Figures 3, 6:
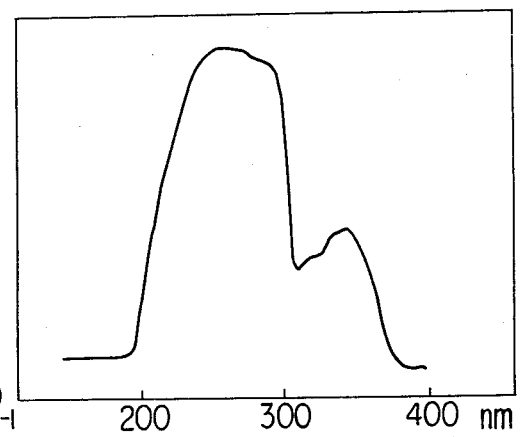

Properties of the compound are given as follows:
PMR: FIG. 6-1

IR: FIG. 6-2
UV: FIG. 6-3
MS: m/e 275

Example VII

A mixture of 452 mg of genipin and 200 mg of aniline was treated in the same manner as in the case of Example III to yield 30 mg of a yellow oily compound.

The compound has the following structural formula:

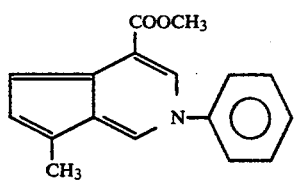

Figures 1, 7:
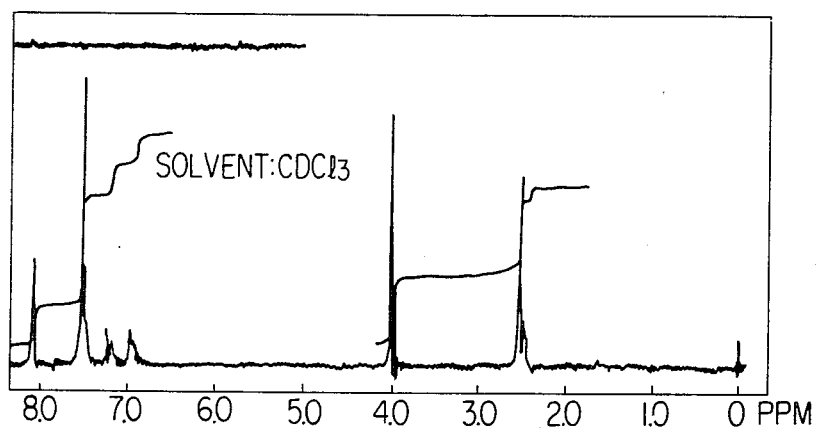

Properties of the compound are given as follows:
PMR: FIG. 7-1

Example VIII

The product obtained in Example II having the structural formula:

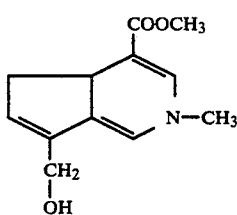

was dissolved in chloroform. The solution was extracted three times with 30 ml. each of 1 N hydrochloric acid. The hydrochloric acid layer was made slightly alkaline with excess aqueous sodium hydroxide and extracted again with chloroform to yield 250 mg of a red oily residue. The residue was applied to a neutral active alumina (activity II) column (40 g, 23×115 mm), which was first eluted with chloroform, then with increasing concentrations of ethanol. Red needles (100 mg) were obtained from the chloroform fraction.

From MP, PMR and IR comparisons, the product was found to be identical with compound of the formula:

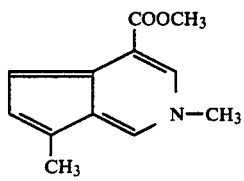

VIII-(1)

obtained in Example III.

Next, 80 mg of a red oily substance was obtained from the ehanol (1%) fraction.

The product was the following structural formula:

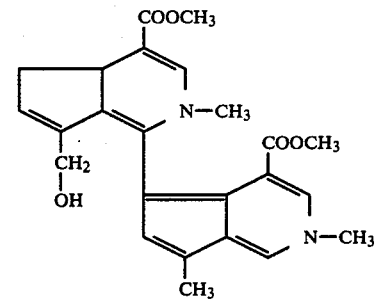

VIII-(2)

Figures 1, 8:
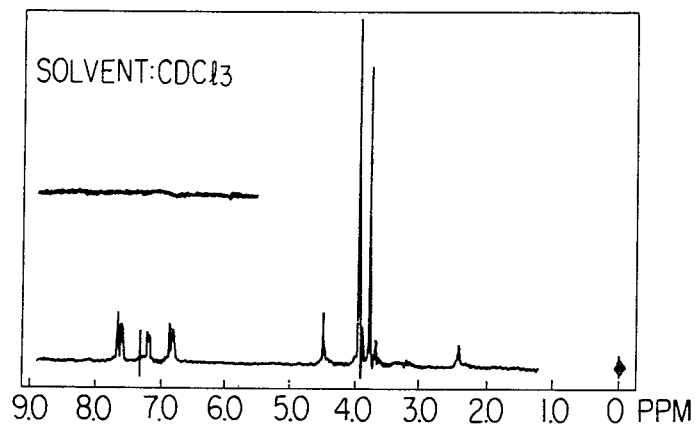
Figures 2, 8:
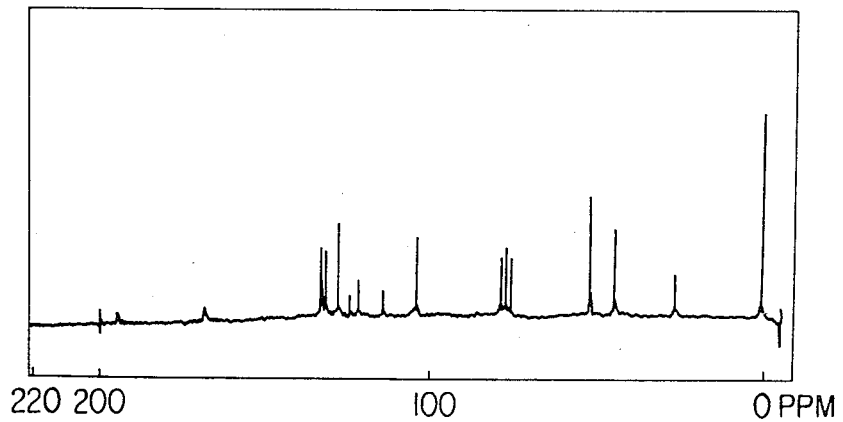
Figures 3, 8:
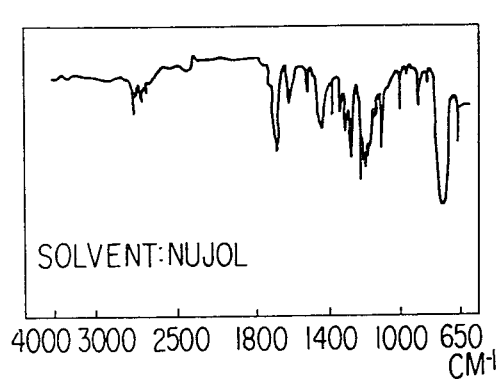
Figures 4, 8:
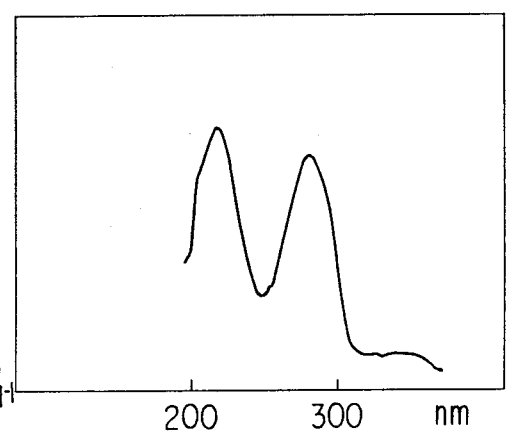
Figures 5, 8:
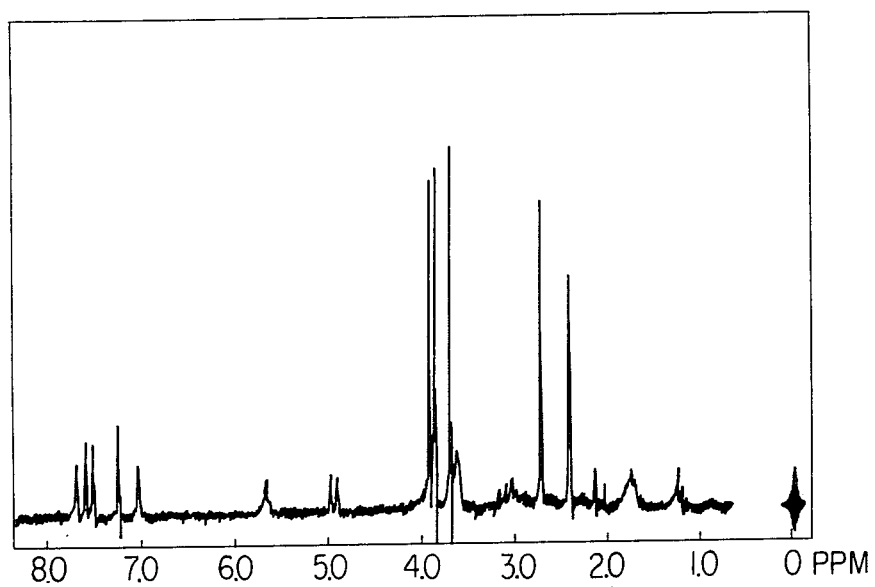
Figures 6, 8:
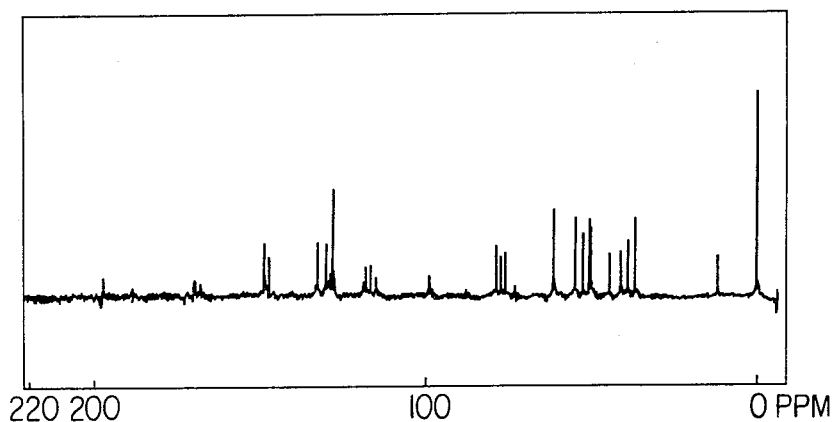
Figures 7, 8:
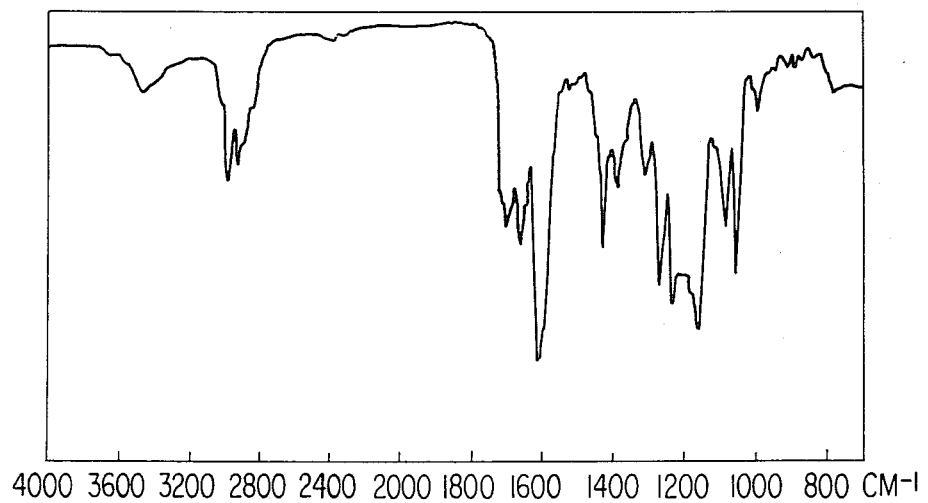
Figure 8:
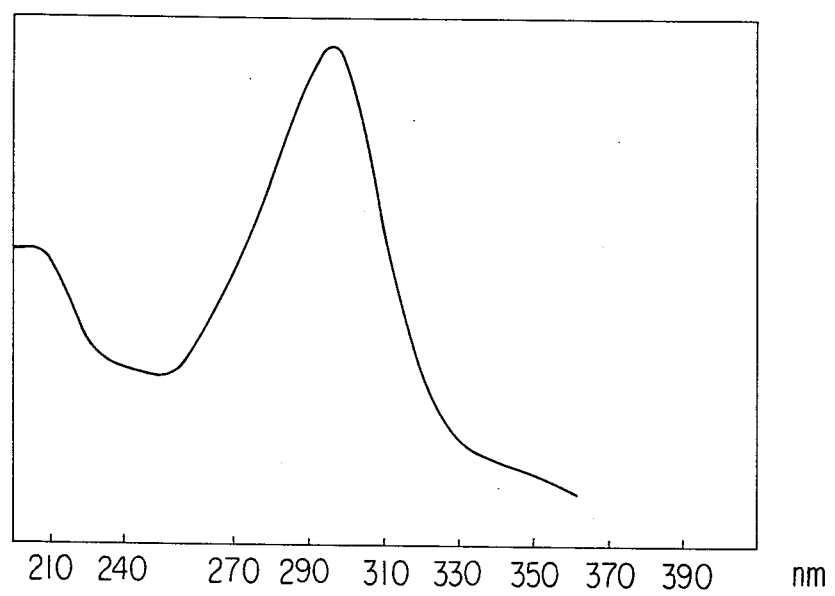

Properties of the compound are given as follows:
PMR: FIG. 8-1
CMR: FIG. 8-2
IR: FIG. 8-3
UV: FIG. 8-4
MS: m/e 404

From PMR and CMR, the product was assigned to be a completely symmetrical dimer.

Further, 15 mg of a red oily substance was obtained from the ethanol (3%) fraction.

The product has the following structural formula:

VIII-(3)

PMR: FIG. 8-5
CMR: FIG. 8-6
IR: FIG. 8-7
UV: $\lambda_{max}^{EtOH}$297 nm(log $\epsilon$=4.19), FIG. 8-8
$[\alpha]_{600}^{25}$ +241° (MeOH, C=0.0704) MS: m/e 424

Example IX

The compound obtained in Example IV (50 mg) was dissolved in 10 ml. of ethanol. The solution was subjected to catalytic reduction over platinum catalyst at room temperature under hydrogen stream for 19 hours. The catalyst was filtered off and then the filtrate was concentrated under reduced pressure. The residue was purified by chromatography on a silica gel column with chloroform as the developing solvent to yield 20 mg of a colorless syrupy reduction product.

The product has the following structural formula:

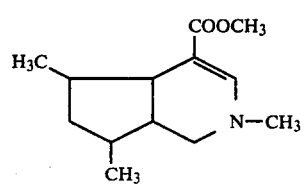

Figures 1, 9:
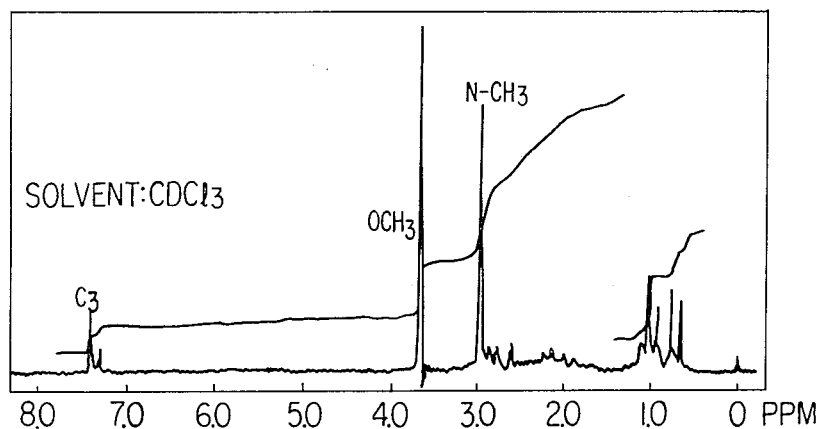
Figures 2, 9:
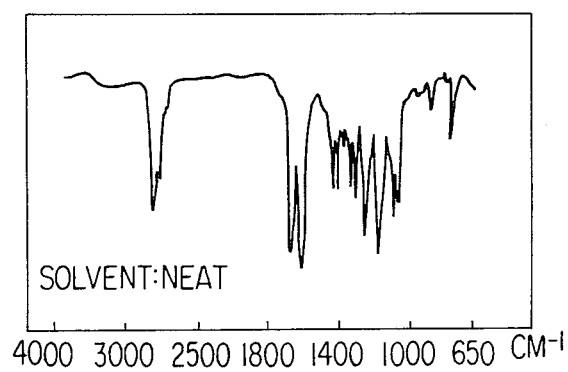

Properties of the compound are given as follows:

PMR: FIG. 9-1
IR: FIG. 9-2
MS: m/e 223

Example X

A mixture of 904 mg of genipin and 268 mg of methylamine hydrochloride was dissolved in 60 ml. of a mixture of McIlvaine buffer solution (pH 7.2) and ethanol (1:1). The solution was stirred at 40°–50° C. under nitrogen stream for one hour. The solvent was evaporated under reduced pressure. The residue was extracted with chloroform. The chloroform extract was washed with water, dried over anhydrous magnesium sulfate and concentrated under reduced pressure. The resulting red syrupy residue was purified by column chromatography on a silical gel column with chloroform as the developing solvent. The chloroform eluates were combined and concentrated under reduced pressure. The resulting residue (250 mg) was subjected to chromatography on a column of Sephadex LH 20 with methanol as the developing solvent. The eluate was concentrated under reduced pressure. The resulting residue was purified by chromatography on a column of active alumina (activity II) with chloroform as the developing solvent. From the chloroform eluate, 70 mg of an orange oily product was obtained. From PMR and IR, the product was found to be identical with the compound of the following structural formula obtained in Example VIII-(2):

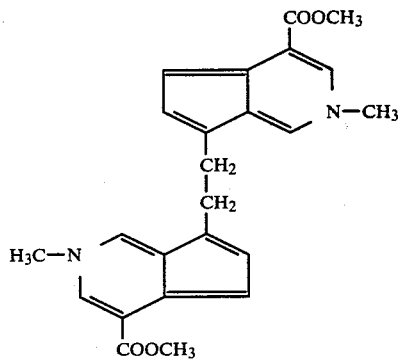

Example XI

A mixture of 904 mg of genipin and 268 mg of methylamine hydrochloride was treated in the same manner as in the case of Example III and then subjected to chromatography on a column of Sephadex LH 20 with methanol as the developing solvent to yield 40 mg of a red oily compound. The product has the following structural formula:

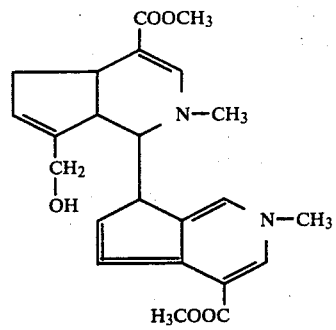

Figures 1, 10:
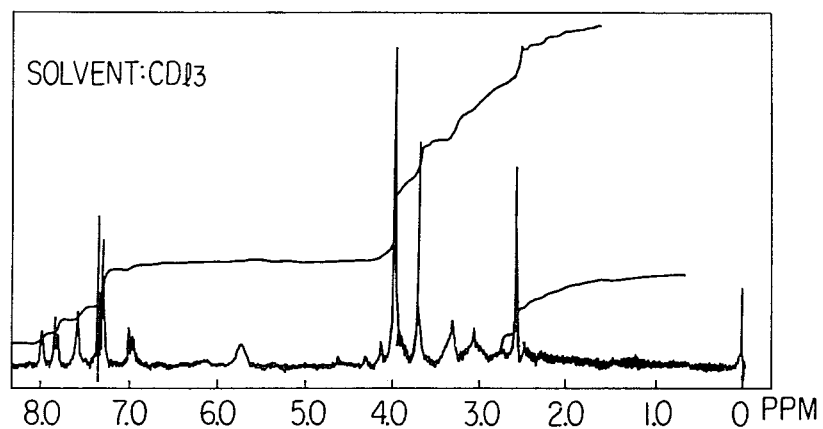
Figures 2, 10:
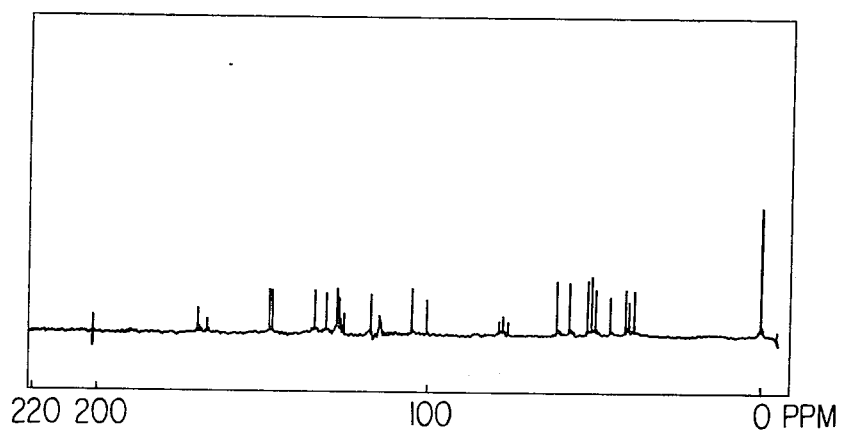
Figures 3, 10:
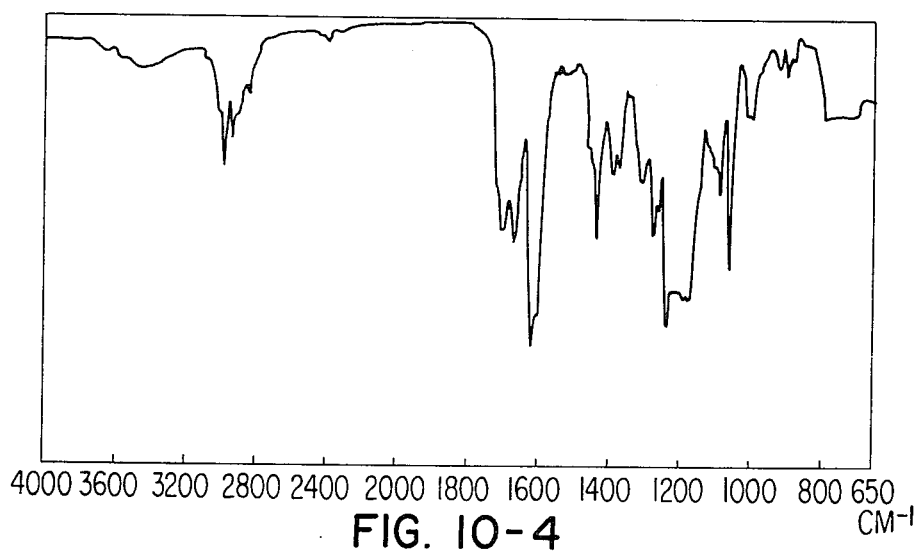
Figures 4, 10:
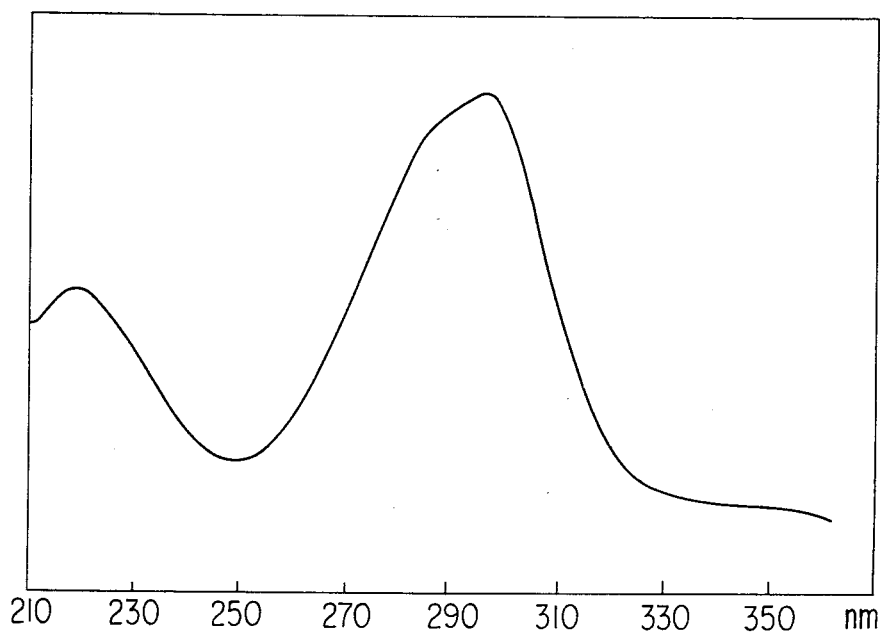

Properties of the compound are given as follows:
PMR: FIG. 10-1
CMR: FIG. 10-2
IR: FIG. 10-3
UV: $\lambda_{max}^{EtOH}$ 296 nm (log $\epsilon$=4.52), FIG. 10-4
MS: m/e 410
$[\alpha]_{650}^{25}$ +43° (MeOH, C=0.175)

Example XII

A mixture of 452 mg of genipin and 134 mg of methylamine hydrochloride was dissolved in a mixture of McIlvaine buffer (pH 6.7) and ethanol (2:1). Air was bubbled into solution at 60°–70° C. for 15 minutes. Then, the solvent was evaporated under reduced pressure. The residue was extracted with chloroform. The chloroform extract was washed with water and dried over anhydrous magnesium sulfate. Then, the solvent was evaporated under reduced pressure to yield 300 mg of a red syrupy residue. The residue was subjected to chromatography on a silica gel column with ether-methanol as the developing solvent. Fraction of an eluate (ether: methanol = 85:15) yielded 80 mg of an oily compound.

The compound has the following structural formula:

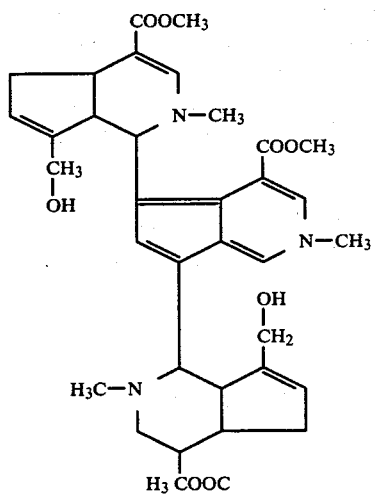

Figures 1, 11:
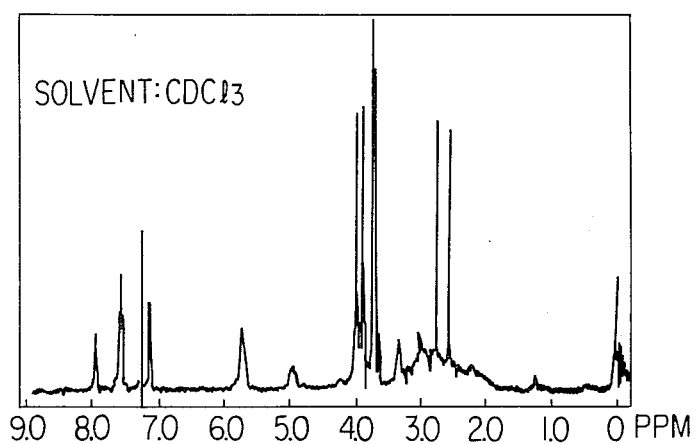
Figures 2, 11:
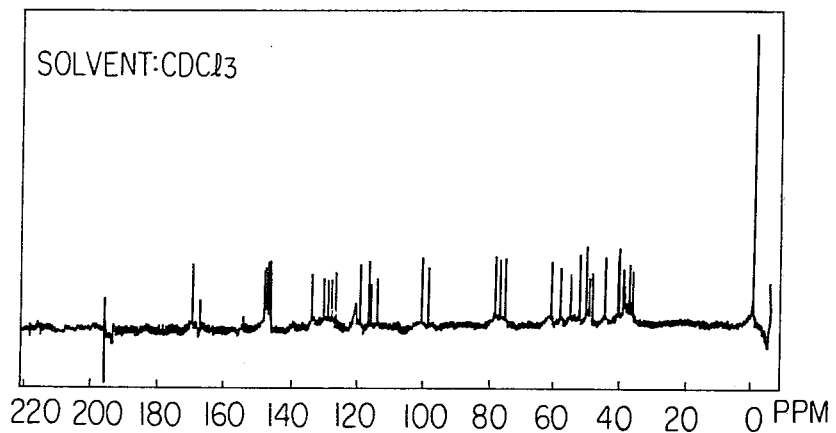
Figures 3, 11:
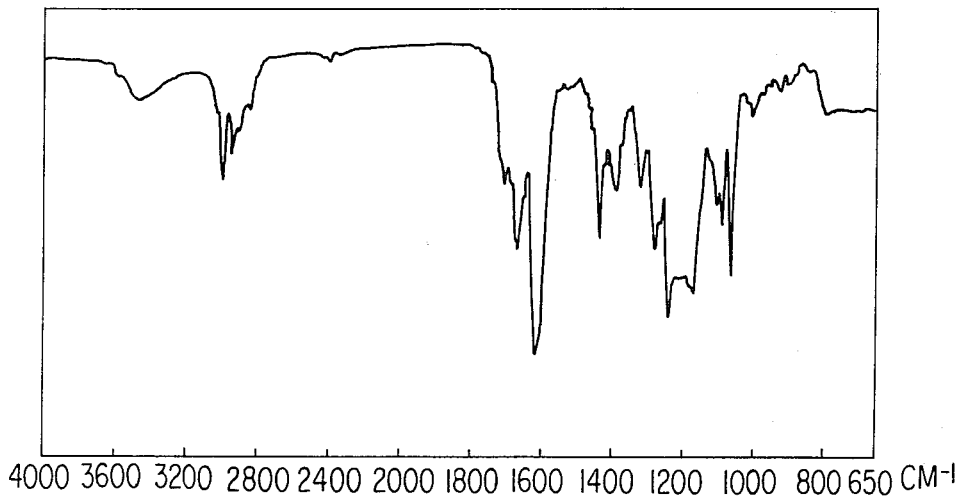
Figures 4, 11:
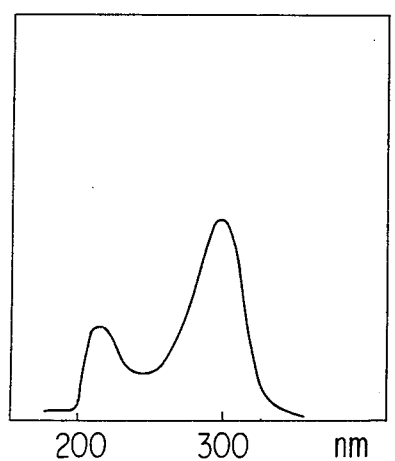

Properties of the compound are given as follows:
PMR: FIG. 11-1
CMR: FIG. 11-2
IR: FIG. 11-3
UV: $\lambda_{max}^{EtOH}$ 297 nm (log $\epsilon$=4.69), FIG. 11-4
MS: m/e 631
$[\alpha]_{650}^{25}$ +202° (MeOH, C=0.0593)

Example XIII

A mixture of 452 mg (2 mM) of genipin and 402 mg (6 mM) of methylamine hydrochloride was dissolved in 40 ml. of a mixture of McIlvaine buffer (pH 7.2) and ethanol (1:1). After heating to 70° C. under argon, the product was extracted with chloroform to yield 420 mg of a red oily residue. The residue was subjected to chromatography on a column (40 g, 23×115 mm) of neutral active alumina (activity II), and eluted first with chloroform, then with increasing concentrations of ethanol. Each fraction was further subjected to purification by preparative thin-layer chromatography. From PMR and IR, it was confirmed that compounds of the following structural formulae were produced:

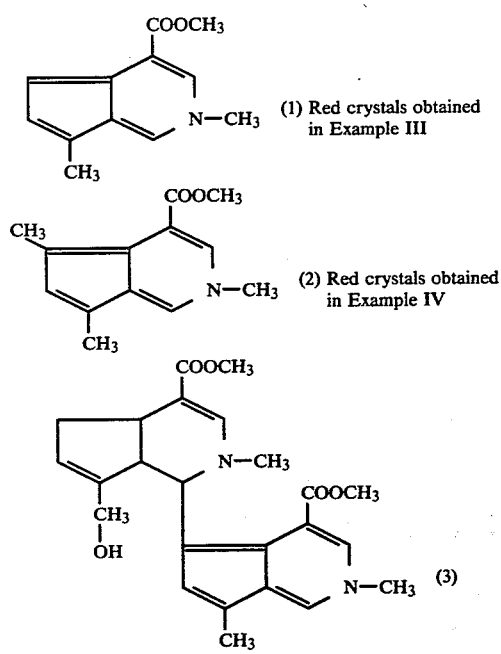

Figures 1, 12:
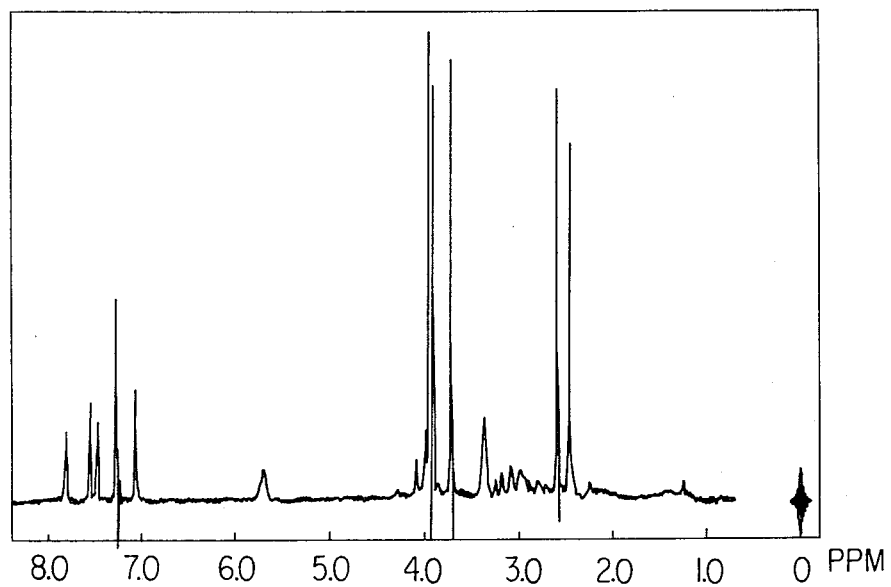
Figures 2, 12:
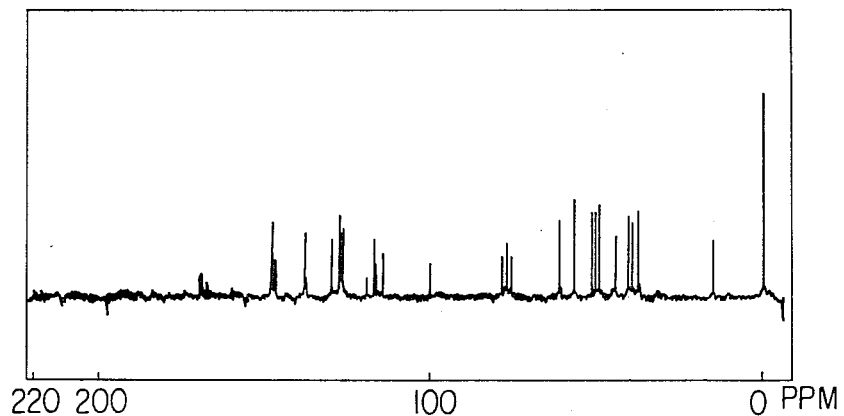
Figures 3, 12:
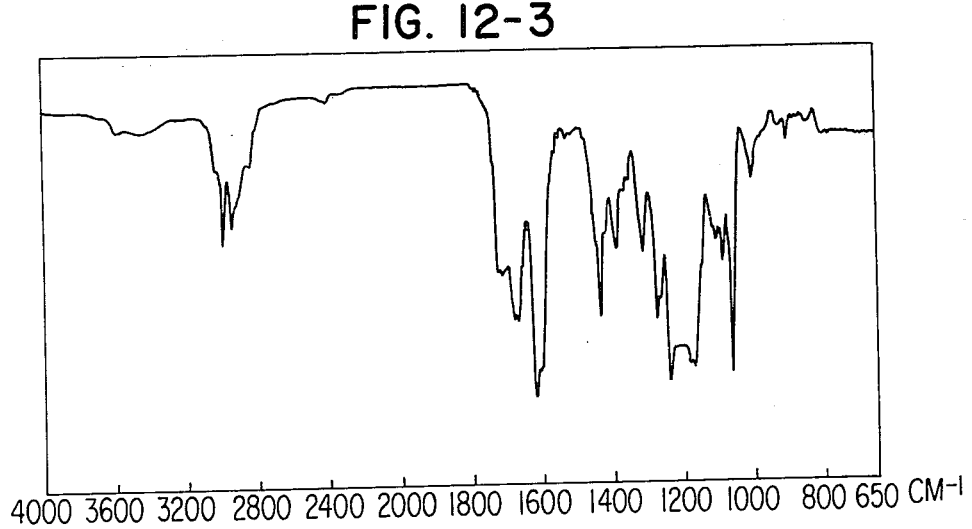
Figures 4, 12:
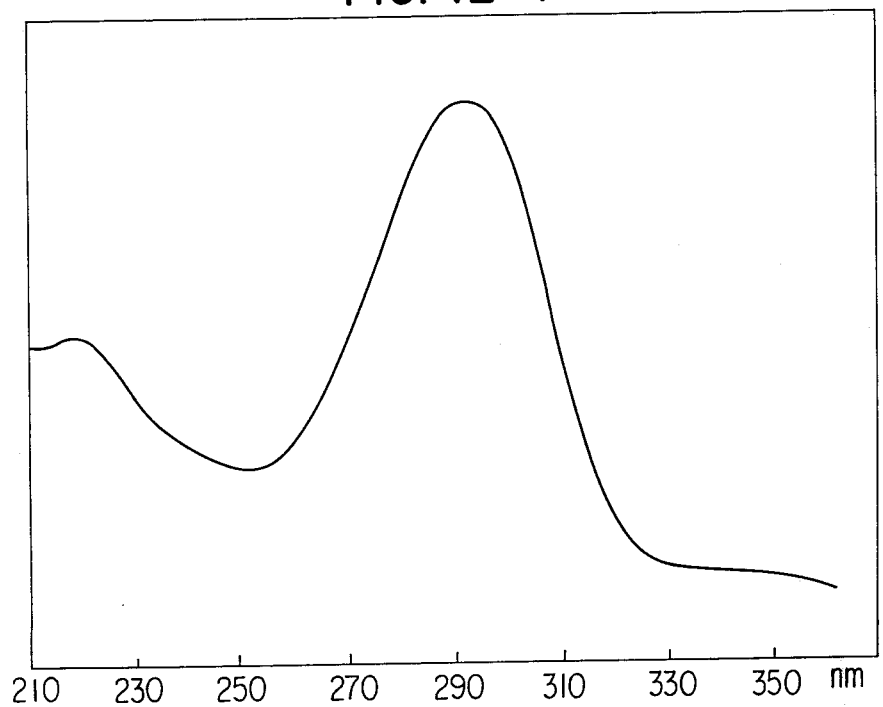
Figures 1, 13:
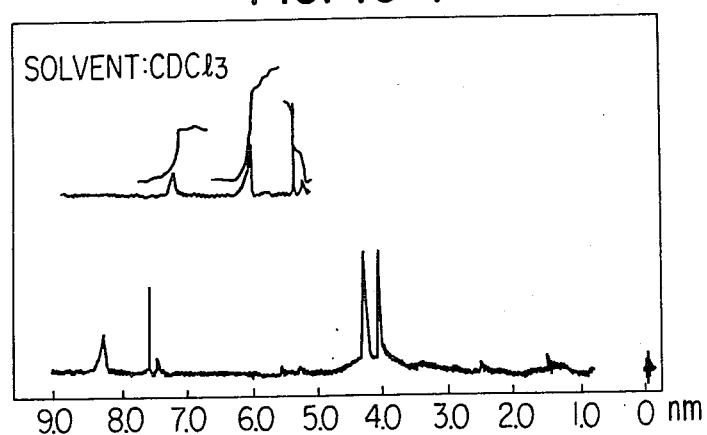
Figures 2, 14:
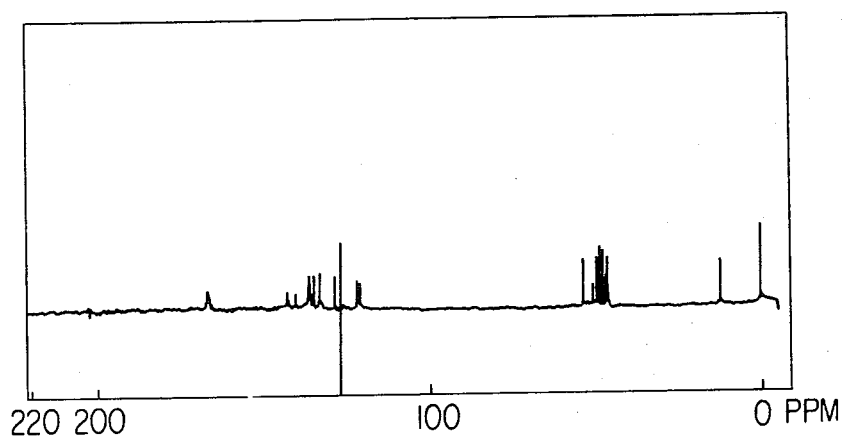
Figures 3, 14:
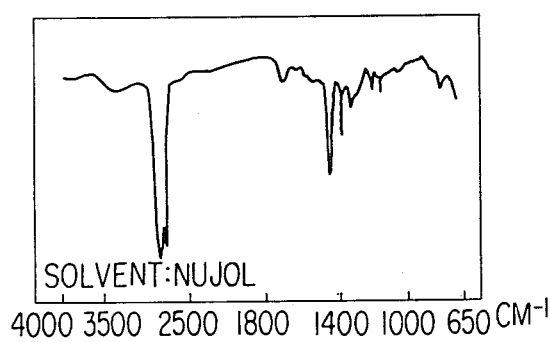
Figures 4, 14:
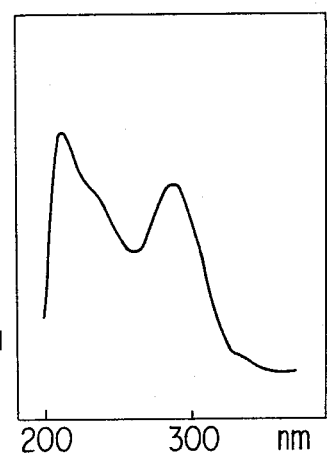
Figures 5, 14:
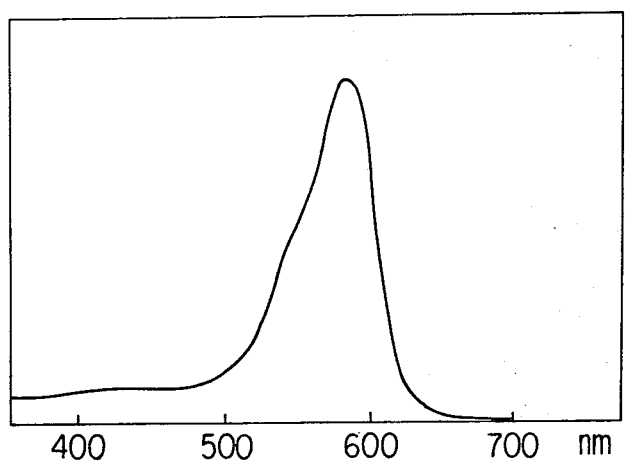

PMR: FIG. 12-1
CMR: FIG. 12-2
IR: FIG. 12-3
UV: $\lambda_{max}^{EtOH}$ 292 nm (log $\epsilon$=4.51), FIG. 12-4
MS: m/e 424
$[\alpha]_{650}^{25}$ +22° (MeOH, C=0.202)

This substance is considered to be stereoisomeric at the binding site between the monomer units of the dimer obtained in Example VIII-(3).

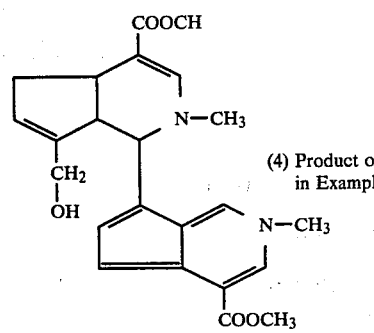

(4) Product obtained in Example XI

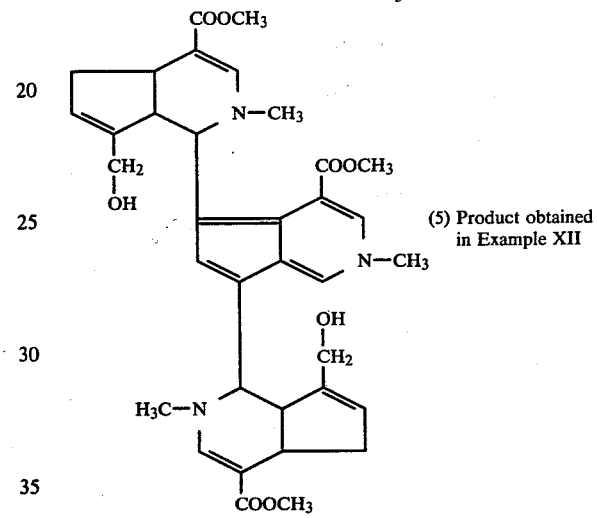

(5) Product obtained in Example XII

Example XIV

The product obtained in Example XII (90 mg) was dissolved in 20 ml. of aqueous ethanol (1:1). The solution was stirred under nitrogen for 5 hours at 70°–80° C. Then, the solvent was evaporated under reduced pressure. The resulting residue was subjected to preparative thin-layer chromatography with ether as the developing solvent to give three products [yields: (1) 3 mg, (2) 12 mg and (3) 3 mg]. From PMR and IR, the products were confirmed to be compounds of the following structural formulae:

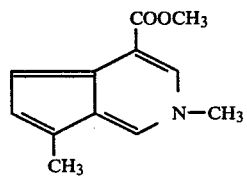

(1) Product obtained in Example III

-continued
(2) Product obtained in Example XI
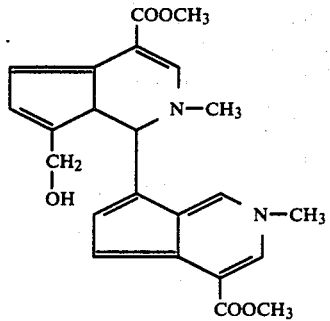
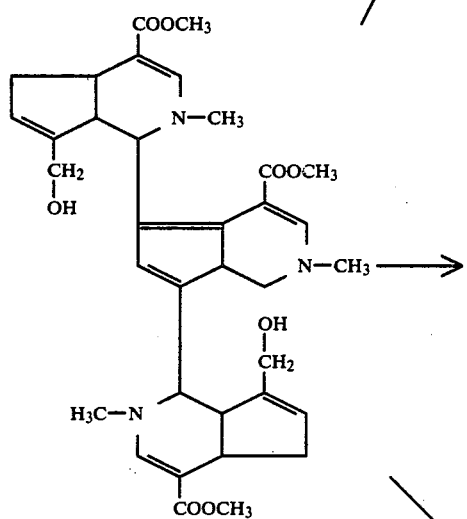
(3) Product obtained in Example XIII
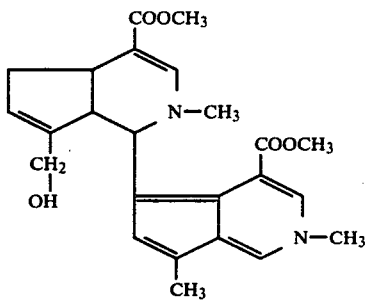
Example XV
The product of Example XI (100 mg) was subjected to reaction in the same manner as in the case of Example XIV to give two products [yields: (1) 5 mg and (2) 15 mg]. From PMR and IR, the products were confirmed to be compounds of the following structural formualae:
(1) Product obtained Example III
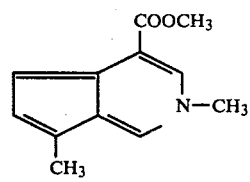

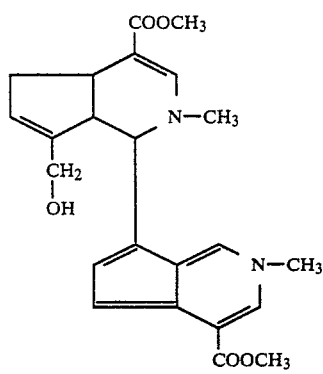

-continued (2) Product obtained in Example XII

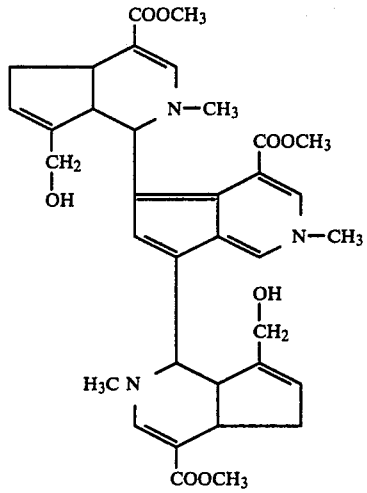

Example XVI

The product of Example VIII-(3) (75 mg) was subjected to reaction in the same manner as in the case of Example XIV to give two compounds [yields: (1) 7 mg and (2) 5 mg]. From PMR and IR, the products were confirmed to be compounds of the following structural formulae:

Example XVII

The product of Example X (100 mg) was dissolved in 30 ml. of 50% aqueous methanol. The solution was stirred in an open system at room temperature for 24 hours and concentrated under reduced pressure to yield 90 mg of a purple syrupy residue. The residue was purified by chromatography on an active alumina (activity III) column with chloroform as the solvent. A bluish (1) Product obtained in Example III

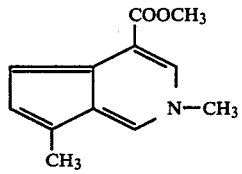

(2) Product obtained in Example XII

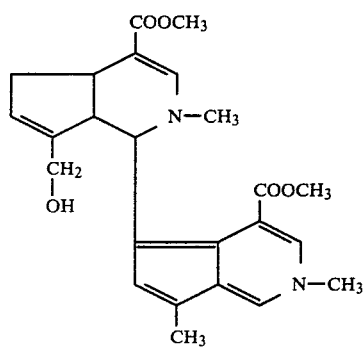

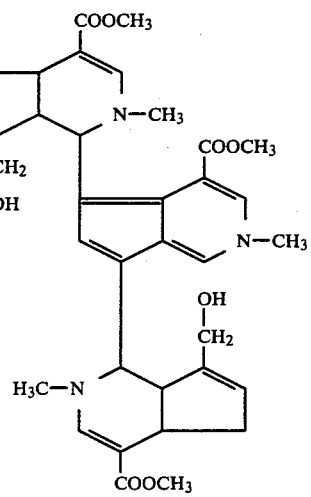

purple syrupy product (30 mg) was obtained from an eluate of chloroform: methanol=95:5.

The product has the following structural formula:

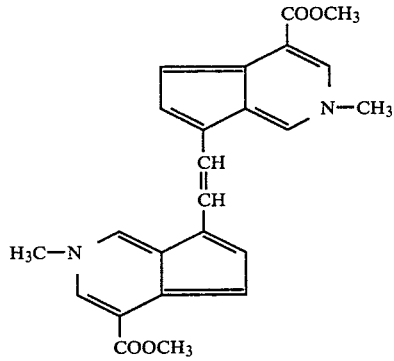

Properties of the compound are given as follows:

PMR: FIG. 13-1

IR: FIG. 13-2

UV: FIG. 13-3

VIS: FIG. 13-4

MS: m/e 402

Example XVIII

The compound obtained in Example IV was dissolved in 30 ml. of 50% aqueous methanol. The solution was stirred at 60°–70° C. in the air for 5 hours and then concentrated under reduced pressure to yield 70 mg of a bluish purple syrupy residue. The residue was purified by chromatography on an active alumina column (activity III) with chloroform as the developing solvent. A blue syrupy product (30 mg) was obtained from an eluate of chloroform: methanol=90:10.

The product has the following structural formula:

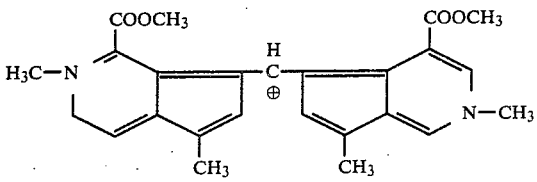

Properties of the compound are given as follows:

PMR: FIG. 14-1

CMR: FIG. 14-2

VIS: FIG. 14-5

We claim:

1. Nitrogen-containing monoterpene derivatives of the general formulae:

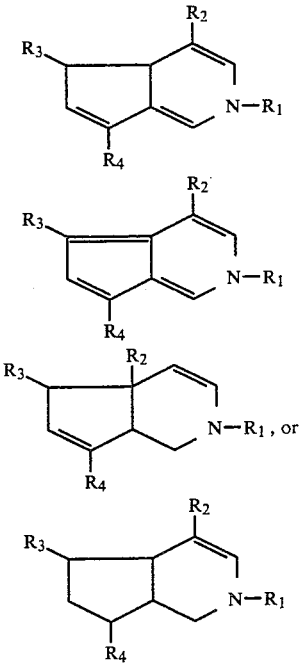

wherein:

$R_1$ represents a lower alkyl group, phenyl, lower alkyl group containing carboxylic acid or its ester, $R_2$ represents —COOH or —COOR, wherein R represents a lower alkyl group, $R_3$ represents hydrogen or a lower alkyl group, and $R_4$ represents a lower alkyl group or —CH$_2$OH.

* * * * *

UNITED STATES PATENT AND TRADEMARK OFFICE
CERTIFICATE OF CORRECTION

PATENT NO. : 4,232,159
DATED : November 4, 1980
INVENTOR(S) : Ryousuke TOUYAMA et al It is certified that error appears in the above—identified patent and that said Letters Patent is hereby corrected as shown below:

Column 14, lines 28-40, formula VIII-(3) should read as follows:

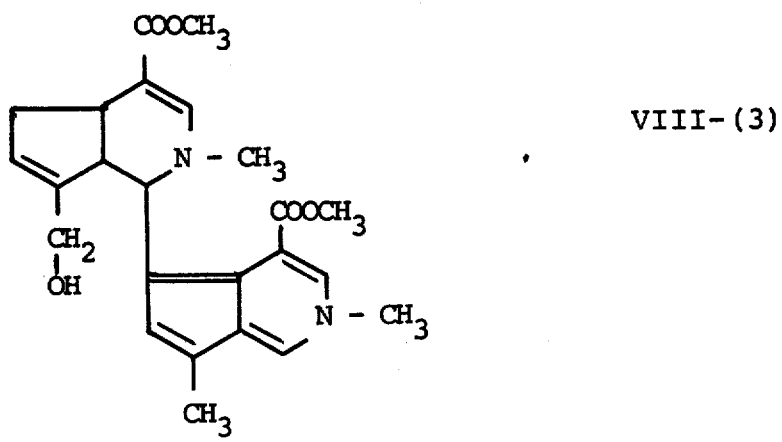

VIII-(3)

UNITED STATES PATENT AND TRADEMARK OFFICE
CERTIFICATE OF CORRECTION

PATENT NO. : 4,232,159   Page 2 of 7
DATED : November 4, 1980
INVENTOR(S) : Ryousuke TOUYAMA et al It is certified that error appears in the above—identified patent and that said Letters Patent is hereby corrected as shown below:

Column 16, lines 1-15, the formula should read as follows:

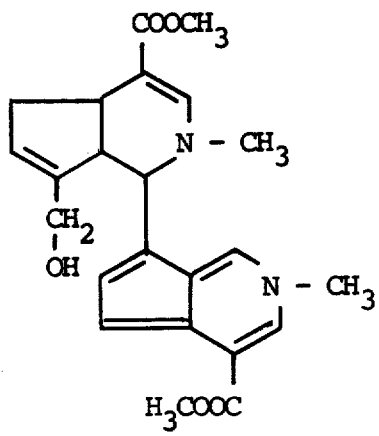

UNITED STATES PATENT AND TRADEMARK OFFICE
CERTIFICATE OF CORRECTION

PATENT NO.  : 4,232,159                             Page 3 of 7
DATED       : November 4, 1980
INVENTOR(S) : Ryousuke TOUYAMA et al It is certified that error appears in the above—identified patent and that said Letters Patent is hereby corrected as shown below:

Column 16, lines 40-60, the formula should read as follows:

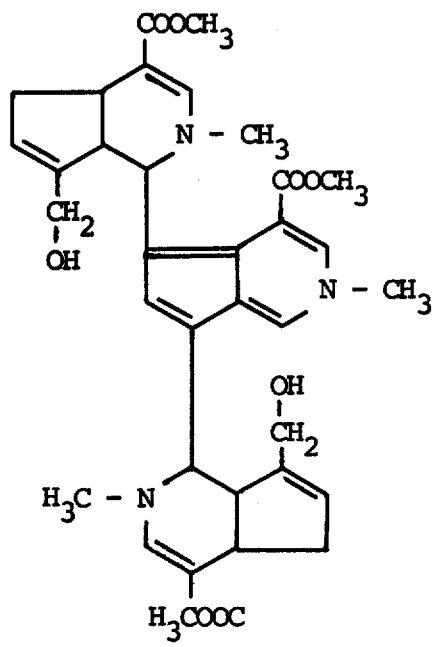

UNITED STATES PATENT AND TRADEMARK OFFICE
CERTIFICATE OF CORRECTION

PATENT NO. : 4,232,159
DATED : November 4, 1980
INVENTOR(S) : Ryousuke TOUYAMA et al It is certified that error appears in the above—identified patent and that said Letters Patent is hereby corrected as shown below:

Column 17, lines 30-40, formula (3) should read as follows:

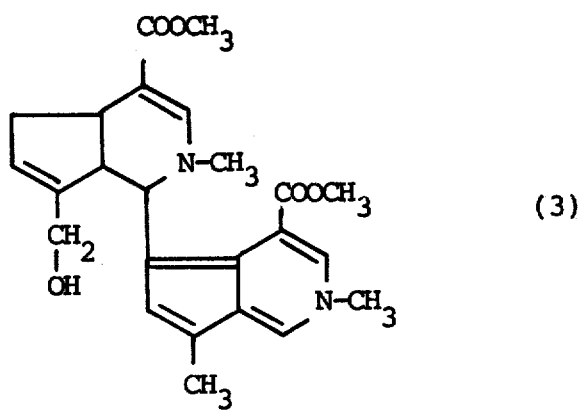

UNITED STATES PATENT AND TRADEMARK OFFICE
CERTIFICATE OF CORRECTION

PATENT NO. : 4,232,159
DATED : November 4, 1980
INVENTOR(S) : Ryousuke TOUYAMA et al It is certified that error appears in the above—identified patent and that said Letters Patent is hereby corrected as shown below:

Column 18, lines 5-16, formula (4) should read as follows:

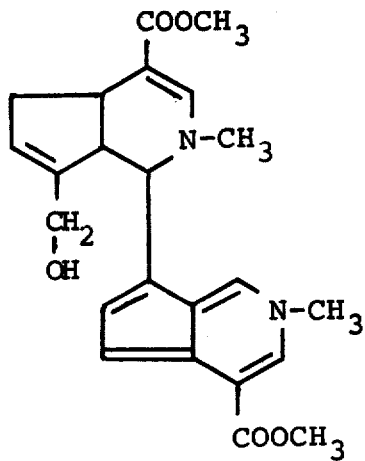

(4) Product obtained in Example XI

UNITED STATES PATENT AND TRADEMARK OFFICE
CERTIFICATE OF CORRECTION

PATENT NO. : 4,232,159
DATED : November 4, 1980
INVENTOR(S) : Ryousuke TOUYAMA et al It is certified that error appears in the above—identified patent and that said Letters Patent is hereby corrected as shown below:

Columns 19 and 20, lines 1-25, should read as follows:

(2) Product obtained in Example XI

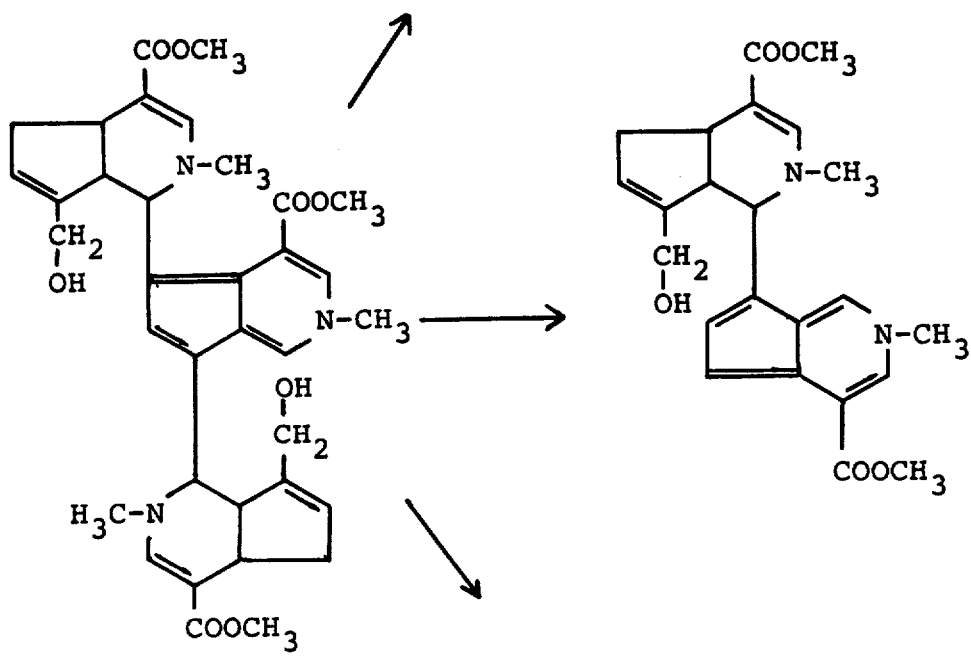

UNITED STATES PATENT AND TRADEMARK OFFICE
CERTIFICATE OF CORRECTION

PATENT NO. : 4,232,159
DATED : November 4, 1980
INVENTOR(S) : Ryousuke TOUYAMA et al It is certified that error appears in the above—identified patent and that said Letters Patent is hereby corrected as shown below:

Column 24, lines 1-10, the formula should read as follows:

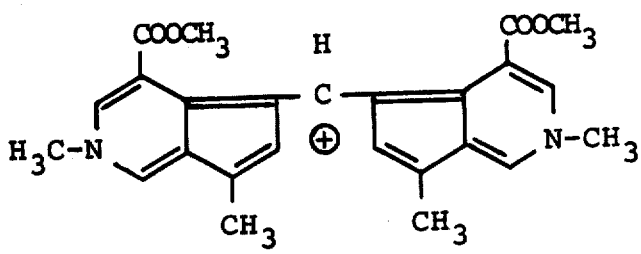

Signed and Sealed this

Twelfth Day of January 1982

[SEAL]

Attest:

Attesting Officer

GERALD J. MOSSINGHOFF

Commissioner of Patents and Trademarks